United States Patent
Ohodnicki, Jr. et al.

(10) Patent No.: US 10,345,279 B1
(45) Date of Patent: *Jul. 9, 2019

(54) PALLADIUM AND PLATINUM-BASED NANOPARTICLE FUNCTIONAL SENSOR LAYERS AND INTEGRATION WITH ENGINEERED FILTER LAYERS FOR SELECTIVE H2 SENSING

(71) Applicant: Energy, United States Department of, Washington, DC (US)

(72) Inventors: Paul R Ohodnicki, Jr., Alison Park, PA (US); Chenhu Sun, South Park, PA (US); John P Baltrus, Jefferson Hills, PA (US); Thomas D Brown, Finleyville, PA (US)

(73) Assignee: U.S. Department of Energy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/641,193

(22) Filed: Jul. 3, 2017

Related U.S. Application Data

(63) Continuation-in-part of application No. 14/887,660, filed on Oct. 20, 2015, now Pat. No. 9,696,256.

(Continued)

(51) Int. Cl.
    *G01N 33/00*     (2006.01)
    *G01N 21/47*     (2006.01)
    *G01N 21/59*     (2006.01)

(52) U.S. Cl.
    CPC ........... *G01N 33/005* (2013.01); *G01N 21/47* (2013.01); *G01N 21/59* (2013.01)

(58) Field of Classification Search
    CPC .... G01N 21/47; G01N 21/554; G01N 33/005; G01N 21/59

(Continued)

(56) References Cited

U.S. PATENT DOCUMENTS 9,696,256 B1 * 7/2017 Ohodnicki, Jr. ..... G01N 21/554

* cited by examiner

*Primary Examiner* — Tri T Ton
(74) *Attorney, Agent, or Firm* — Timothy L. Harney; Michael J. Dobbs; Brian J. Lally

(57) ABSTRACT

The disclosure relates to a method for $H_2$ sensing in a gas stream utilizing a hydrogen sensing material. The hydrogen sensing material is comprised of Pd-based or Pt-based nanoparticles having an average nanoparticle diameter of less than about 100 nanometers dispersed in an inert matrix having a bandgap greater than or equal to 5 eV, and an oxygen ion conductivity less than approximately $10^{-7}$ S/cm at a temperature of 700° C. Exemplary inert matrix materials include $SiO_2$, $Al_2O_3$, and $Si_3N_4$ as well as modifications to modify the effective refractive indices through combinations and/or doping of such materials. Additional exemplary matrix materials consist of zeolitic and zeolite-derivative structures which are microporous and/or nanoporous such as the alumino-silicates and the dealuminated zeolite NaA structures. Additional sensing layers may be comprised of (1) a single "nanocomposite" layer comprised of Pd- or Pt-based particles dispersed within an inert matrix, (2) multi-layered sensing layers comprised of a nanocomposite layer with a filter overlayer, (3) core-shell layers comprised of matrix materials surrounding a core of Pd-based or Pt-based nanoparticles, and any combinations of the above.

24 Claims, 21 Drawing Sheets

Related U.S. Application Data

(60) Provisional application No. 62/065,964, filed on Oct. 20, 2014.

(58) Field of Classification Search
USPC .................................................. 356/337–343
See application file for complete search history.

FIG. 14A
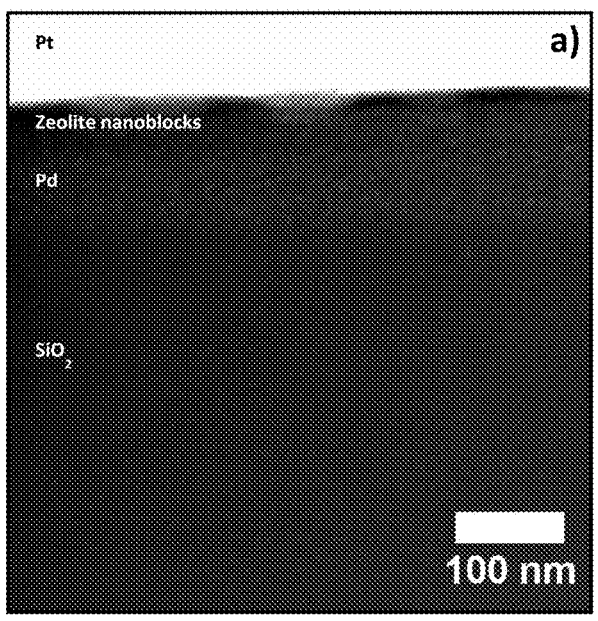
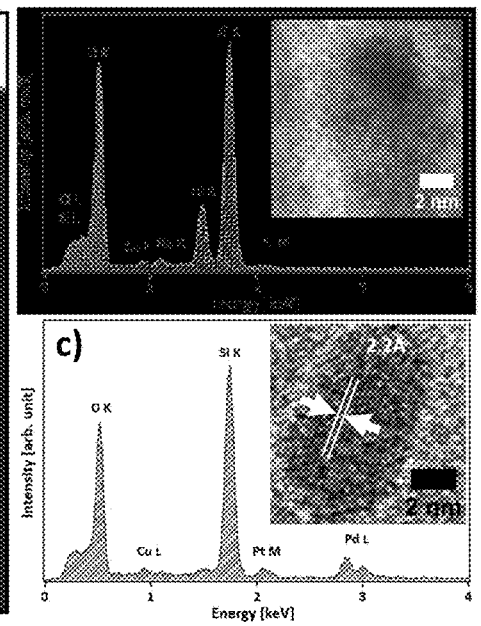
FIG. 14B
FIG. 14C

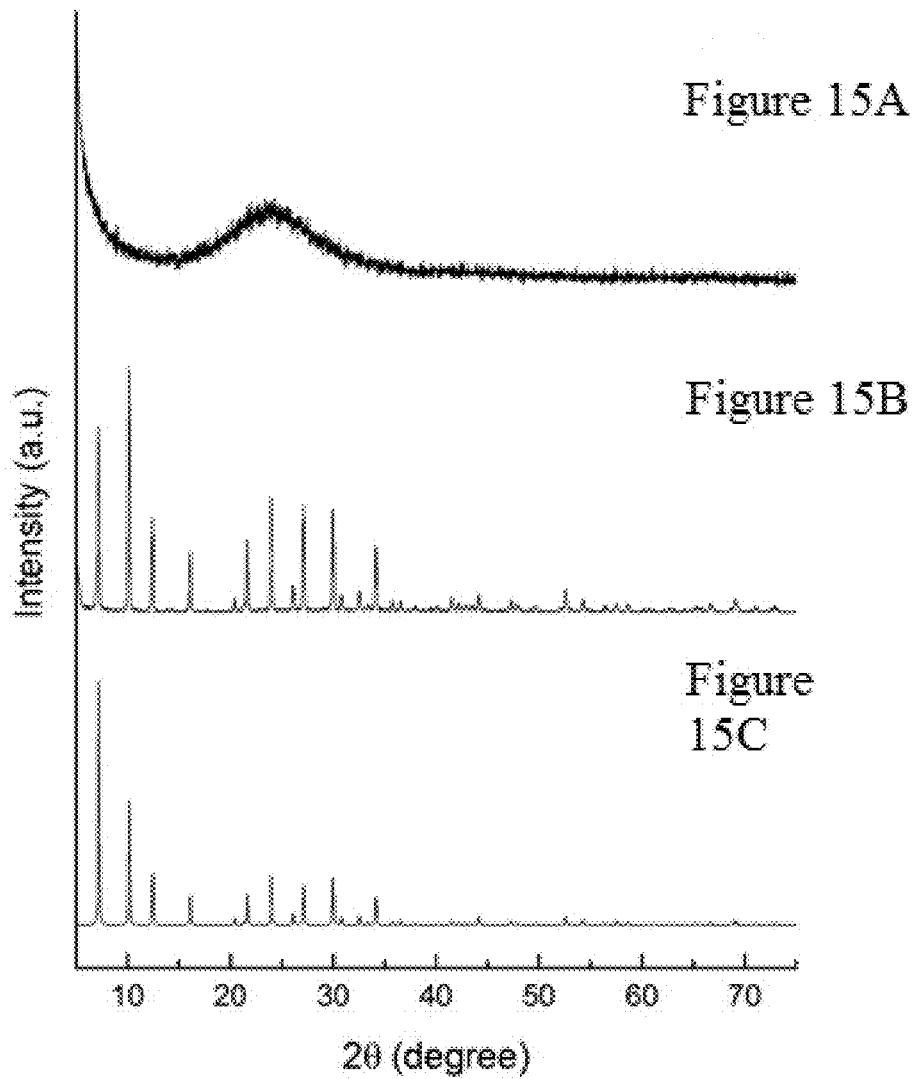

PALLADIUM AND PLATINUM-BASED NANOPARTICLE FUNCTIONAL SENSOR LAYERS AND INTEGRATION WITH ENGINEERED FILTER LAYERS FOR SELECTIVE H2 SENSING

RELATION TO OTHER APPLICATIONS

This patent application is a continuation-in-part of and claims priority from U.S. patent application Ser. No. 14/887,660 filed Oct. 20, 2015, which is hereby incorporated by reference, which in turn claims priority form provisional patent application 62/065,964 filed Oct. 20, 2014, which is hereby incorporated by reference.

GOVERNMENT INTERESTS

The United States Government has rights in this invention pursuant to the employer-employee relationship of the Government to the inventors as U.S. Department of Energy employees and site-support contractors at the National Energy Technology Laboratory.

FIELD OF THE INVENTION

One or more embodiments relates to a method for sensing the $H_2$ concentration of a gaseous stream through evaluation of the optical signal of a hydrogen sensing material comprised of Pd- or Pt-based nanoparticles dispersed in a matrix material. In many embodiments, the sensing layers are also comprised of engineered filter layers as the matrix or as an additional layer to improve $H_2$ selectivity.

BACKGROUND

The ability to selectively sense $H_2$ is critically important for a broad range of applications spanning energy, defense, aviation, and aerospace. One of the most significant needs is for sensors that are capable of leak detection of $H_2$ at levels up to the lower explosive limit (~4% in ambient air). A large body of work therefore exists focused on the research and development of sensors for $H_2$ leak detection and safety applications with a number of commercial products available on the market. Additional applications of hydrogen sensors requiring operation at elevated temperatures include monitoring of hydrogen in metallurgical processes as well as monitoring the composition of fuel gas streams in power generation technologies such as gas turbines and solid oxide fuel cells. Measurements of $H_2$ levels dissolved in transformer oil can also enable condition-based monitoring to provide early detection of potential failures with large associated economic and environmental impacts. A broad range of sensor devices and technologies have been applied to hydrogen sensing including chemi-resistive, electrochemical, catalytic, work function, acoustic, and optical-based approaches.

Optical-based sensors are particularly well-suited for $H_2$ sensing due to a number of inherent advantages that include elimination of electrical wiring and contacts at the sensing location, which provides benefits in terms of safety and sensor longevity in potentially explosive atmospheres, harsh environments, and at high temperatures. A large number of optical-based hydrogen sensor devices have been developed and demonstrated, many of which are based upon the changes in optical properties of a functional sensor material. Pd and Pd-alloy thin films are the most common materials employed for optical $H_2$ sensing applications due to a well-known dependence of the optical constants of Pd on ambient $H_2$ concentration. See e.g., Vargas et al., "Optical and electrical properties of hydrided palladium thin films studied by an inversion approach from transmittance measurements," Thin Solid Films 496 (2006); see also Silva et al., "A Review of Palladium-Based Fiber-Optic Sensors for Molecular Hydrogen Detection," *IEEE Sensors Journal*, 12(1) (2012); see also Yang et al., "Fiber Optic Hydrogen Sensors: a Review," *Phototonic Sensors* 4(4) (2014), among others. These measurable dependences arise from a large solid solubility of hydrogen ions in the Pd lattice resulting in (1) volume expansion, (2) modifications to free carrier concentration, and (3) alterations to electronic band structure. The overall result is a decrease in the magnitude of the real and imaginary parts of the dielectric constant with increasing $H_2$ in the ambient atmosphere. Pd thin films have also been used in conjunction with optical fibers in an evanescent wave absorption spectroscopy based approach allowing for direct monitoring of changes in the real and imaginary parts of the refractive index. See e.g., Luna-Moreno et al., "Optical fiber hydrogen sensor based on core diameter mismatch and annealed Pd—Au thin films," *Sensors and Actuators B* 125 (2007); see also Wei et al., "Nano-structured Pd-long period fiber gratings integrated optical sensor for hydrogen detection," *Sensors and Actuators B* 134 (2008), among others. In many cases, Pd alloys have shown advantageous sensing properties relative to elemental Pd due to improved film morphology stability and a reduction in (1) hysteresis, (2) response time, and (3) interference due to other chemical species present by suppressing a phase transformation to the $PdH_x$ phase and also tailoring the surface chemistry. See e.g., Luna-Moreno et al, "Tailored Pd—Au layer produced by conventional evaporation process for hydrogen sensing," Optics and Lasers in Engineering 49 (2011), among others.

In more recent work, it has been demonstrated that Pd or Pd-alloy nanoparticles on the surface of silica substrates or unclad optical fibers can also be utilized for optical $H_2$ sensing. For example, AuPd alloy nanoparticles deposited on single-mode fibers mechanically-thinned to 5- or 10-microns in diameter have shown rapid and monotonic responses to $H_2$ at levels up to the lower explosive limit. See Monzon-Hernandez et al., "Optical microfibers decorated with PdAu nanoparticles for fast hydrogen sensing," *Sensors and Actuators B* 151 (2010). In this case, the sensing response was attributed to changes in the effective refractive indices of the particles resulting in a $H_2$-concentration dependent light scattering that increased with increasing $H_2$ concentration at an interrogation wavelength of 1550 nm. Pd nanoparticles on the surface of silica glass substrates have also been synthesized through dewetting of continuous films by high temperature annealing and found to respond optically to $H_2$ when measured in a transmission geometry. See Kracker et al., "Optical hydrogen sensing with modified Pd-layers: A kinetic study of roughened layers and dewetted nanoparticle films," *Sensors and Actuators B* 197 (2014). In addition to reversible $H_2$ responses that are presumably associated with modifications to the optical constants of Pd due to H atoms dissolved into the Pd lattice, this work also demonstrated an irreversible change in transmission upon the first $H_2$ exposure that was claimed to be due to reduction of the Pd-nanoparticles oxidized during high temperature annealing. Pd nanoparticle-based $H_2$ sensing layers have a number of potential advantages as compared to continuous thin films of Pd such as (1) response time, (2) sensitivity, and (3) stability of the microstructure at high temperatures or during $H_2$ loading and unloading cycles. Promising early results have been obtained for such systems but additional work is required to more fully understand the mechanistic origin of the sensing response and to explore the effects of elevated temperatures and the presence of other common gas species previously reported to impact $H_2$ sensing responses of Pd-based thin films such as $O_2$ and CO.

The concept of applying top filter layers above a functional sensing layer to overcome cross-sensitivity is very appealing in the multicomponent gas mixtures of real applications. See Fleischer et al., "Selective gas detection with high-temperature operated metal oxides using catalytic filters," *Sensors and Actuators B: Chemical*, vol. 69, no. 1, pp. 205-210, 2000. Multilayered thin film systems comprised of nanoparticles embedded in a continuous matrix or nanoparticles with a deposited layer have been employed for optimizing the optical response. See Jiang et al., "Multilayer fiber optic sensors for in situ gas monitoring in harsh environments," *Sensors and Actuators B: Chemical*, vol. 177, pp. 205-212, 2013. Zeolites are microporous aluminosilicate crystals which have been widely used in the size-selective separation of gas molecules in the range of 0.3 to 0.4 nm, such as $CO_2/CH_4$ and $CO_2/N_2$ separations. See Carreon et al., "Alumina-supported SAPO-34 membranes for $CO_2/CH_4$ separation," *Journal of the American Chemical Society*, vol. 130, no. 16, pp. 5412-5413, 2008. However, there are few studies on $H_2$ separations even by the small pore zeolites NaA because the 8-membered ring pores (0.38 nm) are still too large to separate $H_2$ (0.289 nm) from other gas molecules such as $CO_2$ (0.33 nm), $N_2$ (0.364), CO (0.376 nm), $CH_4$ (0.38 nm) based upon their kinetic diameters. See Liu et al., "NaKA sorbents with high $CO_2$-over-$N_2$ selectivity and high capacity to adsorb $CO_2$," *Chemical Communications*, vol. 46, no. 25, pp. 4502-4504, 2010. A recent study provided a simple solution of breaking the structure of zeolites NaA into nano-blocks with smaller size openings by dealumination in acid solutions. See Nishiyama et al., "Hydrogen-permeable membranes composed of zeolite nano-blocks," *Journal of Membrane Science*, vol. 306, no. 1, pp. 349-354, 2007. The spin-coated membrane demonstrated a high selectivity for $H_2/CH_4$, $H_2/N_2$ and $H_2/CO$ separations.

These and other objects, aspects, and advantages of the present disclosure will become better understood with reference to the accompanying description and claims.

SUMMARY

Embodiments relate to a method for $H_2$ sensing in a gas stream by utilizing the shifts in an optical signal generated by a hydrogen sensing material, where the hydrogen sensing material is comprised of a plurality of Pd-based nanoparticles, Pt-based nanoparticles, or a combination thereof dispersed in an inert matrix. The hydrogen sensing material is in contact with gaseous constituents comprising the gas stream and periodically comprised of diatomic hydrogen $H_2$, having a concentration which may vary over time. The optical signal is based on a comparison of incident light illuminating the hydrogen sensing material and exiting light which is transmitted, reflected, scattered or a combination thereof by the hydrogen sensing material.

The disclosure herein provides a hydrogen sensing material comprising a plurality of Pd-based and/or Pt-based particles dispersed in an inert matrix, where the inert matrix has a bandgap greater than or equal to 5 eV and has an oxygen ion conductivity of less than $10^{-7}$ S/cm at a temperature of 700° C. An exemplary matrix material consists of silica, alumina, a mixture of the two (i.e. aluminosilicate) and the corresponding silica and alumina based nitrides. Additional exemplary matrix materials consist of zeolitic and zeolite derivative structures which are microporous and/or nanoporous such as the alumino-silicates and the dealuminated zeolite NaA structure as well as other nanoporous layers often used in applications as filter layers. Sensing layers may be comprised of (1) a single "nanocomposite" layer comprised of Pd- or Pt-based particles dispersed within an inert matrix, (2) multi-layered sensing layers comprised of a nanocomposite layer with a filter overlayer, (3) core-shell layers comprised of matrix materials surrounding a core of Pd-based or Pt-based nanoparticles by encapsulation of nanoparticles in the matrix, and any combinations of the above. The hydrogen sensing material provides inherent advantages including: (1) an inherent filtering function of the inert matrix (particularly for amorphous matrices such as silica and zeolitic-derivative structures such as dealuminated zeolite NaA) allowing for potentially improved $H_2$ selectivity and minimization of cross-sensitivity to other species such as CO, (2) the chemically inert nature of the matrix (e.g. silica) as a protective layer for the embedded nanoparticles making them suitable for applications in harsh environments, (3) a relatively low refractive index of many exemplary matrix materials (e.g. silica, alumina) which is similar to that of the optical fiber core material allowing enhanced compatibility with waveguide-based sensing devices, and (4) the ability to controllably tune the thickness of the sensing layers for sensor response and device optimization.

The hydrogen sensing material is comprised of Pd-based and/or Pt-based nanoparticles having an average nanoparticle diameter of less than about 100 nanometers. The Pd-based nanoparticles comprise palladium (Pd), a palladium alloy, or combinations thereof. In an embodiment, the palladium alloy is a palladium-silver alloy, a palladium-copper alloy, a palladium-platinum alloy, or combinations thereof. Similarly, Pt-based nanoparticles comprise platinum (Pt), a platinum alloy, or combinations thereof. In an embodiment, the platinum alloy is a platinum-silver alloy, a platinum-copper alloy or combinations thereof. The Pd-based and Pt-based nanoparticles are dispersed in an inert matrix having a bandgap greater than or equal to 5 electron volts (eV), and an oxygen ion conductivity of less than approximately $10^{-7}$ S/cm at a temperature of 700° C. Exemplary inert matrix materials include $SiO_2$, $Al_2O_3$, and $Si_3N_4$ as well as derivatives such as $MgF_2$ doped $SiO_2$, and mixtures of $SiO_2/Al_2O_3$. Exemplary inert matrix materials also include zeolitic and zeolite-derivative structures which are microporous and/or nanoporous such as the alumino-silicates and the dealuminated zeolite NaA structures. Sensing layers may be comprised of (1) a single "nanocomposite" layer comprised of Pd- or Pt-based particles dispersed within an inert matrix, (2) multi-layered sensing layers comprised of a nanocomposite layer with a filter overlayer, (3) core-shell layers comprised of matrix materials surrounding a core of Pd-based or Pt-based nanoparticles, and any combinations of the above. In certain embodiments, matrix materials are specifically chosen to optimize the effective refractive index of the hydrogen sensing material for use as gas sensitive cladding layers in optical waveguide based sensors. Negligible changes in refractive index and a limited number of free carriers of the inert matrix are expected in response to $H_2$ such that modifications to the optical characteristics of the Pd-based and Pt-based nanoparticles are dominated by direct interactions between the nanoparticles and the ambient atmosphere. Rather than playing an active role in the gas sensing mechanism, the primary role of the inert matrix is two-fold: (1) to mitigate the coarsening of Pd-based and Pt-based nanoparticles under rigorous high temperature conditions and (2) to tailor the effective refractive index of the nanocomposite thin film for optimized sensing response when integrated with an optical waveguide based sensing platform. In many cases, the matrix phase will also be selected to improve hydrogen selectivity by inhibiting chemical diffusion of species other than hydrogen thereby preventing them from reaching the surface of embedded Pd-based and Pt-based nanoparticles. An additional advantage of the embedding matrix is the controlled tunability of the density of the particles within the nanocomposite sensing layer as well as the thickness of the effective layer. Such tunability allows for greater flexibility in optimization of the sensing element for a broad range of potential optical sensor devices as compared to the de-wetted Pd nanoparticle based sensing layers reported by previous investigators. In some embodiments, multilayered sensing layers will be employed for the purpose of (1) filtering of undesired species to improve selectivity and/or (2) optimizing the optical response of the multi-layered sensing through taking advantage of the effects of multi-layer sensing layers on the optical response by tailoring the light-matter interactions and the overall response.

The hydrogen sensing material utilized in at least one embodiment may be prepared using means known in the art for the production of nanoparticles dispersed within a supporting matrix including sol-gel based wet chemistry techniques, impregnation techniques, implantation techniques, sputtering techniques, and others. The sensing material may be deposited as a single monolithic layer or through multi-layered deposition involving a single technique or a combination of several film deposition techniques. The sensing material may also be integrated within a multilayered thin film stack for the purpose of optimizing the overall response of a sensor element. Multilayered thin film stacks may also be used for the purpose of filtering to improve selectivity to desired analytes while minimizing interactions and responses associated with undesired analytes. As just one exemplary embodiment described in detail below, CO interferences can be minimized by a zeolite nano-block based filter layer overcoat to improve selective detection of $H_2$ gas by Pd-based sensing layers.

The novel process and principles of operation are further discussed in the following description.

BRIEF DESCRIPTION OF THE DRAWINGS

FIG. 14A illustrates STEM HAADF image showing the cross section of fiber sample including various layers; FIG. 14B illustrates EDS spectra taken from zeolite/$SiO_2$ layer, and the inset shows formation of crystalline zeolite structure; FIG. 14C EDS spectra taken from Pd/$SiO_2$ layer, and the inset shows a Pd nanoparticle.

FIG. 15A illustrates XRD patterns of the zeolite nanoblocks film; FIG. 15B illustrates XRD patterns of NaA zeolite crystals; and FIG. 15C illustrates XRD patterns of simulated LTA zeolites.

DETAILED DESCRIPTION

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide a method for $H_2$ sensing based on the resulting shifts in an optical signal generated by a hydrogen sensing material comprised of Pd-based nanoparticles, Pt-based nanoparticles, or a combination thereof dispersed in an inert matrix.

The disclosure provides a method for $H_2$ sensing in a gas stream by utilizing the shifts in the optical signal generated by a particular hydrogen sensing material. The hydrogen sensing material comprises a plurality of Pd-based nanoparticles, Pt-based nanoparticles, or a combination thereof dispersed in an inert matrix. The Pd-based nanoparticles comprise palladium (Pd), a palladium alloy, or combinations thereof. In an embodiment, the palladium alloy is a palladium-silver alloy, a palladium-copper alloy, a palladium-platinum alloy, or combinations thereof. Similarly, Pt-based nanoparticles comprise platinum (Pt), a platinum alloy, or combinations thereof. In an embodiment, the platinum alloy is a platinum-silver alloy, a platinum-copper alloy or combinations thereof. In an embodiment, a metallic component comprises at least 50 wt. %, preferably at least 70 wt. %, more preferably at least 90 wt. % of the plurality of nanoparticles, where the metallic component consists of one of palladium, platinum, a palladium alloy, a platinum alloy, and combinations thereof. In another embodiment at least 30 wt. % and in a further embodiment at least 50 wt. % of the metallic component consists of palladium, platinum, or combinations thereof. The plurality of Pd and/or Pt-based nanoparticles have an average nanoparticle diameter of less than about 100 nm, and the inert matrix has a bandgap exceeding 5 eV and an oxygen ion conductivity of less than approximately $10^{-7}$ S/cm at a temperature of 700° C. In an embodiment, the plurality of Pd and/or Pt-based nanoparticles have an average nanoparticle diameter of less than about 10 nm.

Figure 1:
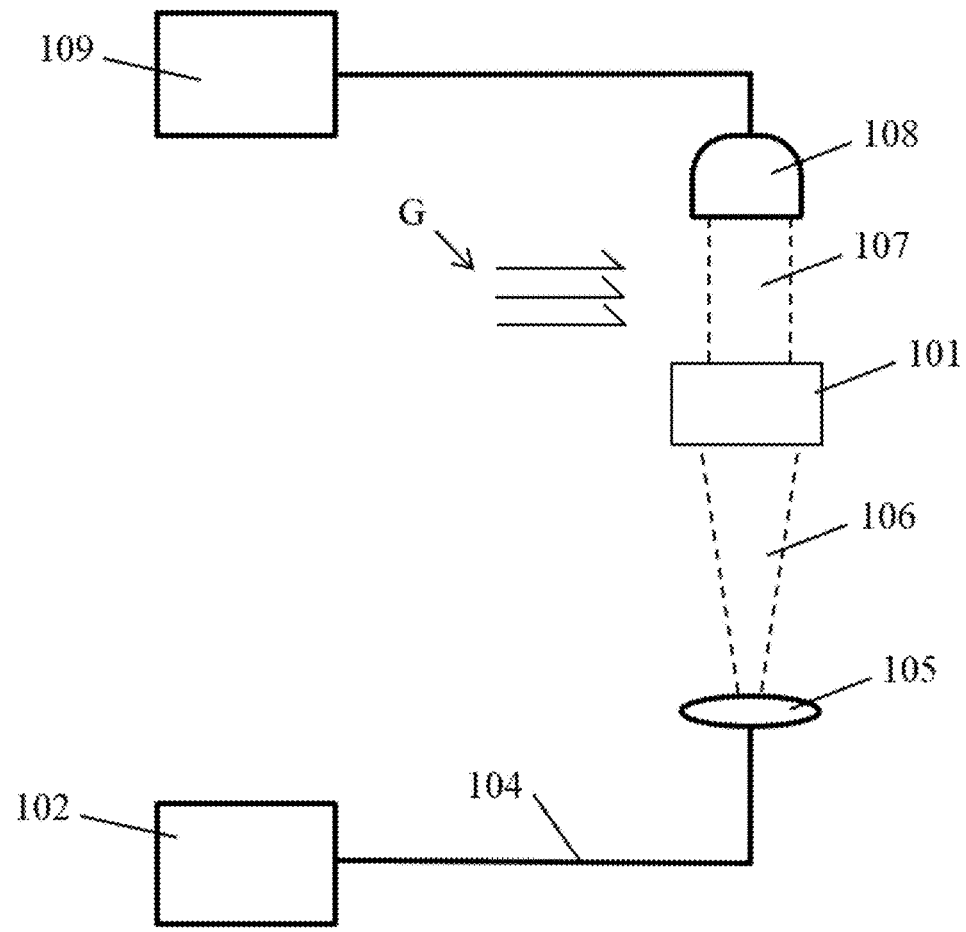
FIG. 1 illustrates a methodology for sensing $H_2$ in a high temperature gas stream using the hydrogen sensing material.

The basic principles of the method are illustrated in FIG. 1. In FIG. 1, light from light source 102 is directed along an optical fiber 104 and focused by lens 105 producing incident light 106 illuminating hydrogen sensing material 101. Concurrently, exiting light 107 is collected behind the specimen using a probe 108 connected to a spectrophotometer 109. Data generated by spectrophotometer 109 or supporting equipment is processed, and an optical signal is displayed. The optical signal is a comparison of the incident light and the exiting light and indicates the absorption, transmission, reflection, and scattering of the incident light at certain wavelengths by hydrogen sensing material 101. The optical signal generally indicates selective photon absorption at certain wavelengths by hydrogen sensing material 101. The hydrogen sensing material 101 is additionally in contact with a gas stream G. Incident light 106, hydrogen sensing material 101, and exiting light 107 generate an optical signal which depends on the hydrogen concentration of the gas stream G, and the optical signal at monitored wavelengths is indicative of the hydrogen concentration and any changes in the hydrogen concentration.

Figure 2:
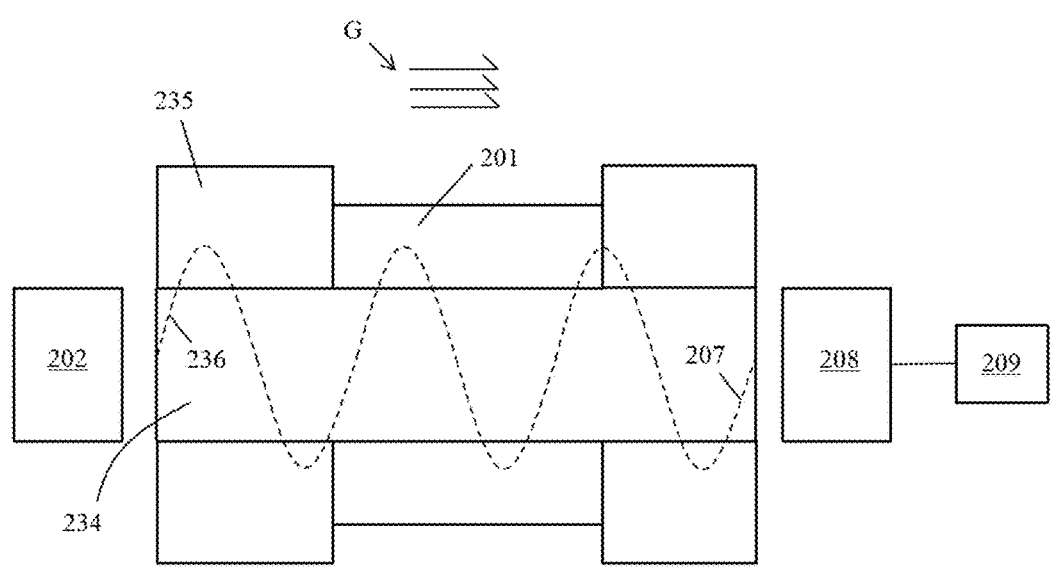
FIG. 2 illustrates a hydrogen sensing material configuration suitable for the detection of $H_2$ using a waveguide sensor.

An additional embodiment is depicted at FIG. 2, where the hydrogen sensing material 201 is illuminated by a wave propagating along a waveguide, such as a fiber optic cable. The waveguide is comprised of a core material 234 in contact with a cladding material 235, where core material 234 has a refractive index greater than cladding material 235. For example, core material 234 and cladding material 235 may be comprised of silica and various additions such as germanium, titanium, phosphorous, boron, fluorine, or other dopants in order to alter the respective refractive indices and meet the necessary criteria. In FIG. 2 light source 202 emits light into core material 234, generating wave 236 penetrating cladding material 235. Additionally in FIG. 2, hydrogen sensing material 201 having the properties disclosed is placed in contact with core material 234 such that hydrogen sensing material 201 is illuminated by wave 236 as incident light, as illustrated. Exiting light 207 is collected by probe 208, connected to spectrophotometer 209. Illumination of hydrogen sensing material 201 by wave 236 enables evaluating the hydrogen concentration of gas stream G in contact with hydrogen sensing material 201 by monitoring a shift in the optical signal, as earlier described. The optical power and penetration depth of wave 236 into cladding 235 and hydrogen sensing material 201 can be described by Beer-Lambert law in many cases. See e.g., Dickinson et al., "Convergent, Self-Encoded Bead Sensor Arrays in the design of an Artificial Nose," *Anal. Chem.* 71 (1999), among others. As is similarly understood, the optical power coupled into the evanescent field may be improved by various methods such as bending, optimizing the relative refractive indices of the core and cladding, use of hollow fibers, and other methods. See e.g., Elosua et al., "Volatile Organic Compound Optical Fiber Sensors: A Review," *Sensors* 6 (2006), among others. Responses that are substantially absent without fiber bending are typically less preferred due to limitations imposed upon optical fiber sensor design and deployment including an ability to perform distributed interrogation.

Figure 3:
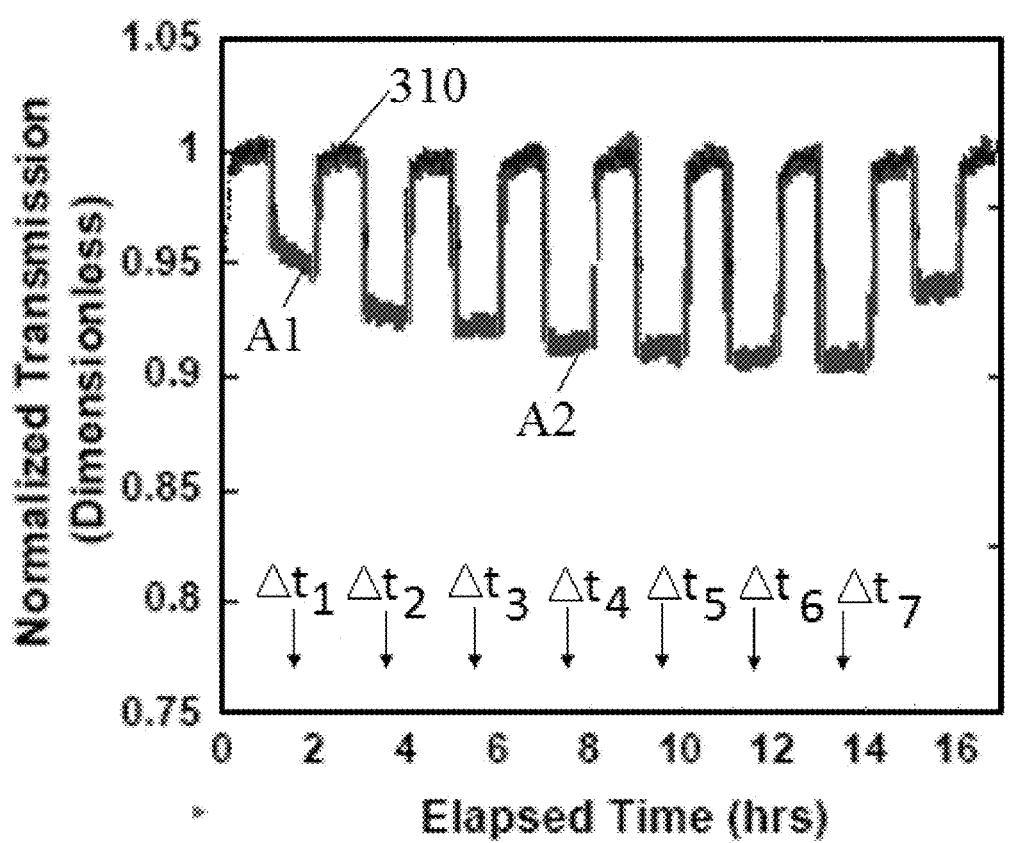
FIG. 3 illustrates an optical signal generated by an embodiment of the hydrogen sensing material.
Figure 4:
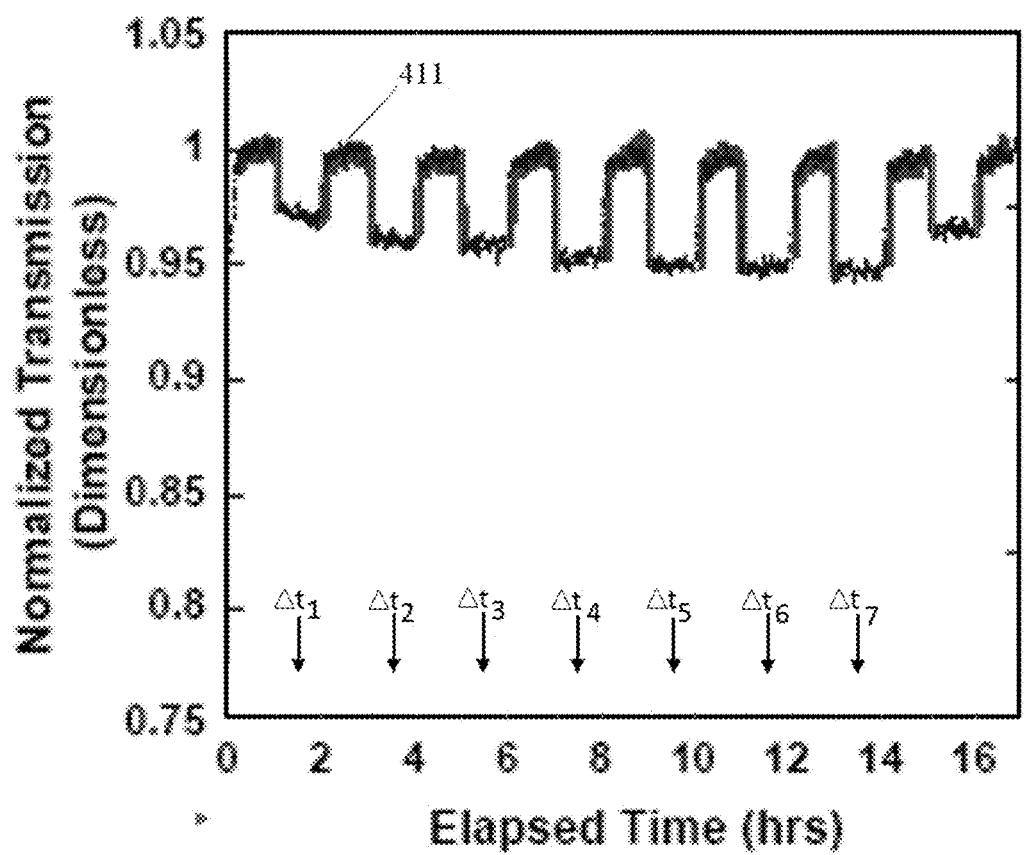
FIG. 4 illustrates an optical signal generated by another embodiment of the hydrogen sensing material.

As an example, FIG. 3 illustrates the results of the method using an apparatus similar to that depicted at FIG. 2, where the hydrogen sensing material comprises Pd-based nanoparticles and a matrix material silica ($Pd/SiO_2$), where the hydrogen sensing material is in contact with a gas stream at room temperature. FIG. 3 illustrates the optical signal 310 as normalized transmission as a function of experiment time. Measured $H_2$ sensing responses are presented for a range of $H_2$ levels from 2% to 100% by volume in a balance of ultra-high purity (UHP) $N_2$, with $H_2$ levels of 2%, 3%, 4%, 10%, 25%, 50%, and 100% over time periods $\Delta t_1$, $\Delta t_2$, $\Delta t_3$, $\Delta t_4$, $\Delta t_5$, $\Delta t_6$, and $\Delta t_7$ respectively. The results show that at room temperature, a monotonic response can be observed over the entire range of $H_2$ levels with sufficiently rapid response and recovery times for practical applications. FIG. 4 illustrates results for a similar $PdAu/SiO_2$ coated optical fiber, illustrating optical signal 411 as normalized transmission with similar $H_2$ levels of 2%, 3%, 4%, 10%, 25%, 50%, and 100% over time periods $\Delta t_1$, $\Delta t_2$, $\Delta t_3$, $\Delta t_4$, $\Delta t_5$, $\Delta t_6$, and $\Delta t_7$ respectively. Similar results are obtained at elevated gas stream temperatures such as 200° C., 400° C., and 600° C. See Ohodnicki et al., "$Pd/SiO_2$ and $AuPd/SiO_2$ nanocomposite-based optical fiber sensors for $H_2$ sensing applications," *Sensors and Actuators B* 214 (2015), which is incorporated by reference.

Within this disclosure, "optical signal" means a comparison of light incident on the $H_2$ sensing material and light exiting the $H_2$ sensing material at one or more wavelengths using optical spectroscopy. Correspondingly, the optical signal may reflect one specific wavelength, or may reflect a monitored band of wavelengths. The optical signal may be expressed as, for example, a transmittance at the one or more wavelengths, an absorption at the one or more wavelengths, or any other parameters which indicate the absorption, transmission, reflection, scattering or other optical impacts on the incident light as a result of interaction with the $H_2$ sensing material. As is understood, optical spectroscopy based on a comparison of the incident light and the exiting light may indicate the absorption, transmission, reflection, scattering, and optical impacts which occur as a result of interaction between the incident light and the $H_2$ sensing material. See e.g., Ingle, James D., and Stanley R. Crouch, Spectrochemical analysis, Englewood Cliffs, N.J.: Prentice Hall, 1988; see also Sole, Jose, *An Introduction to the Optical Spectroscopy of Inorganic Solids* (2005); see also Sarid, Dror and Challener, William, *Modern Introduction to Surface Plasmon: Theory, Mathematica Modeling, and Applications* (2010), among others. Additionally, the optical signal as disclosed here is generally not constrained to a specific wavelength or band of wavelengths. For example, the optical signal may occur at one or more wavelengths typically considered to be ultraviolet, visible, or near-infrared as those terms are used in the art, as well as wavelengths falling outside those delineated ranges.

In prior art, localized surface plasmon resonance (LSRP) based sensing materials have been disclosed such as Au-nanoparticles embedded in an inert matrix of the type disclosed here. See e.g. U.S. Pat. No. 8,741,657 issued to Ohodnicki et al., issued Jun. 3, 2014. For such materials, the chemical sensing response is believed to be associated with a charge transfer between the chemical species to be sensed and the sensing material such that a shift in the LSPR absorption peak of the metallic particles associated with a modified free carrier density of the Au nanoparticles can be resolved. See e.g. Baltrus et al., "Examination of charge transfer in Au/YSZ for high-temperature optical gas sensing," *Applied Surface Science* 313 (2014). In the sensing materials disclosed here, the changes in optical response are typically associated with direct absorption of $H_2$ within the Pd-based and Pt-based nanoparticle lattice resulting in modifications to the effective optical constants of Pd-based and Pt-based nanoparticles. Such mechanisms result in an enhanced selectivity relative to charge transfer-based responses due to the specific affinity of Pd and Pd-based as well as Pt and Pt-based alloys for high levels of $H_2$ dissociation and absorption within the crystalline lattice. See e.g. Ohodnicki et al., *Sensors and Actuators B* 214 (2015). In some cases, responses for Pd-based and Pt-based nanoparticles may also be associated with modifications to the oxidation state which is not observed for Au-LSPR based sensing materials due to their relatively high degree of nobility. In cases where it is desired for oxidation to be minimized, Pt-based nanoparticles may be employed due to the higher nobility as compared to Pd-based nanoparticles.

Figure 5:
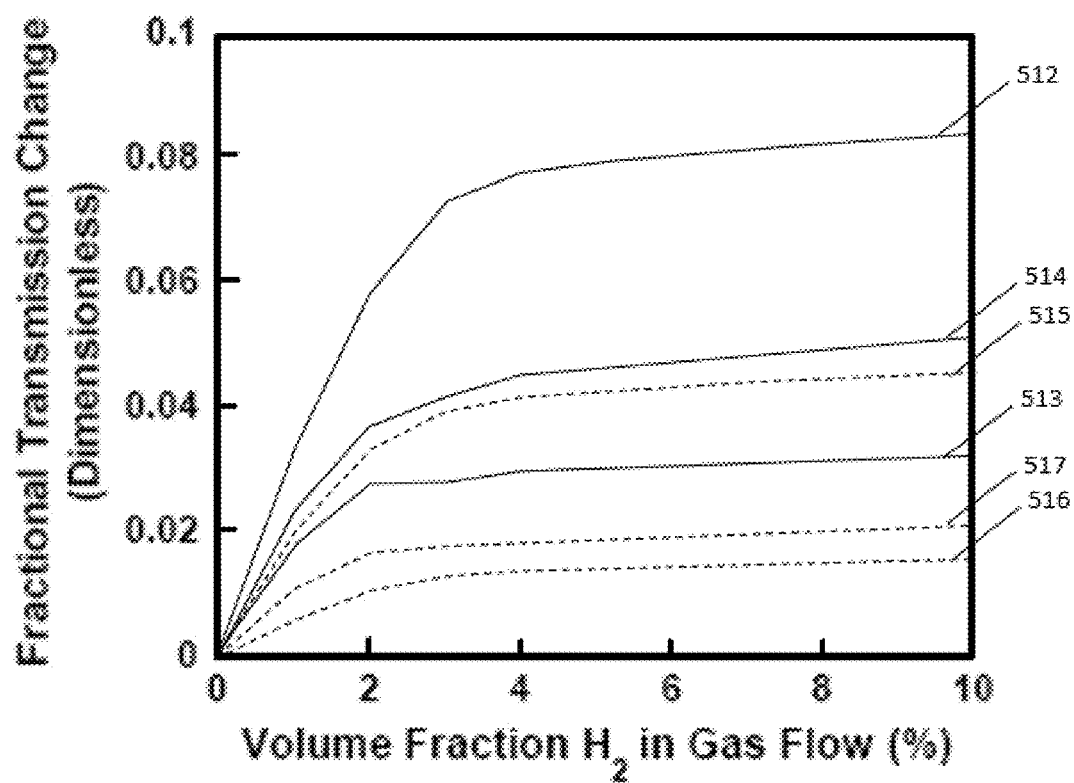
FIG. 5 illustrates performance of the hydrogen sensing material over a range of $H_2$ concentrations.
Figure 6:
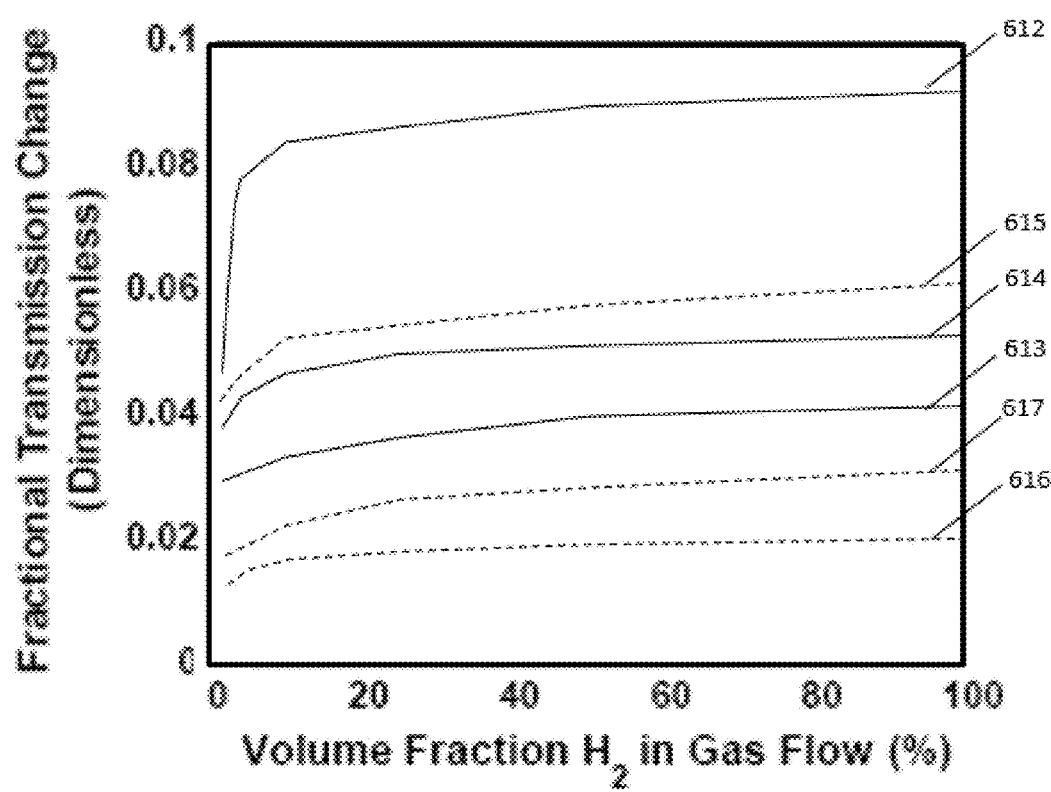
FIG. 6 illustrates performance of the hydrogen sensing material over another range of $H_2$ concentrations.

As additional examples, optical signals as a function of $H_2$ concentration in the gas stream are summarized at FIGS. 5 and 6 for varying temperatures. FIG. 5 illustrates $H_2$ sensing response for both $Pd/SiO_2$ and $AuPd/SiO_2$ materials at lower $H_2$ concentrations, where optical signals 512, 513, and 514 represent the response for the $Pd/SiO_2$ material at room temperature, 200° C., and 400° C. respectively versus the $H_2$ concentrations shown, and optical signals 515, 516, and 517 represent the response for the $AuPd/SiO_2$ material at room temperature, 200° C., and 400° C. respectively versus the $H_2$ concentrations shown. Similarly, FIG. 6 illustrates $H_2$ sensing response for both $Pd/SiO_2$ and $AuPd/SiO_2$ materials for $H_2$ concentrations up to 100%, where optical signals 612, 613, and 614 represent the $Pd/SiO_2$ material at room temperature, 200° C., and 400° C. respectively, and optical signals 615, 616, and 617 represent the $AuPd/SiO_2$ material at room temperature, 200° C., and 400° C. respectively.

Figure 7:
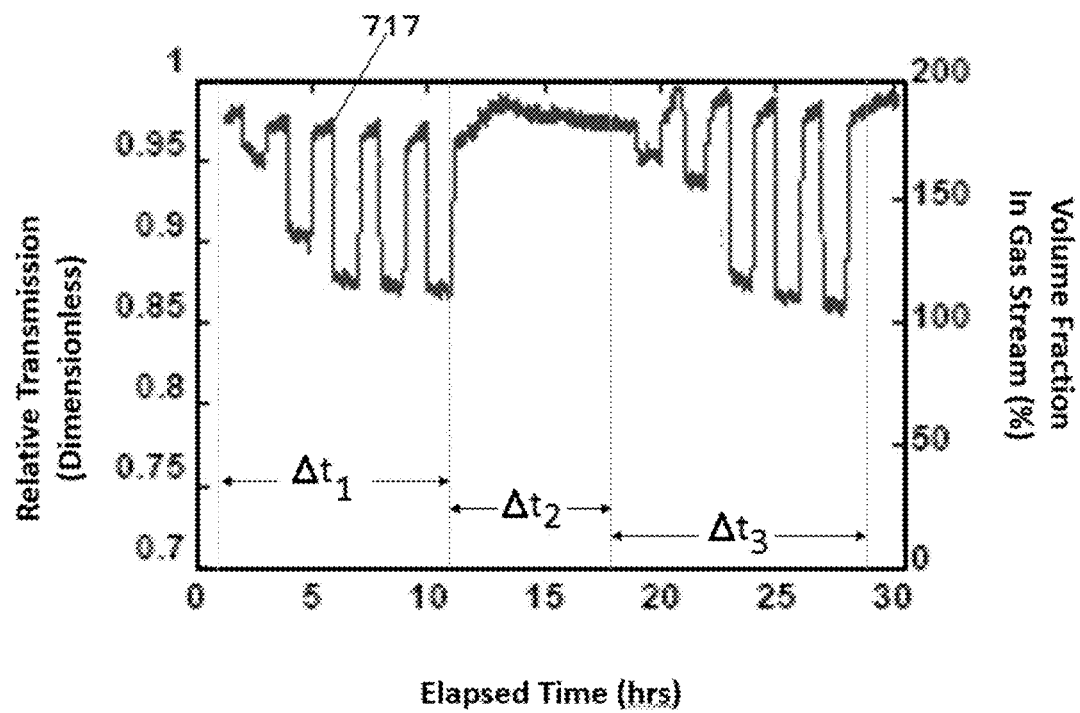
FIG. 7 illustrates an optical signal in the presence of $H_2$, CO, and $O_2$.
Figure 8:
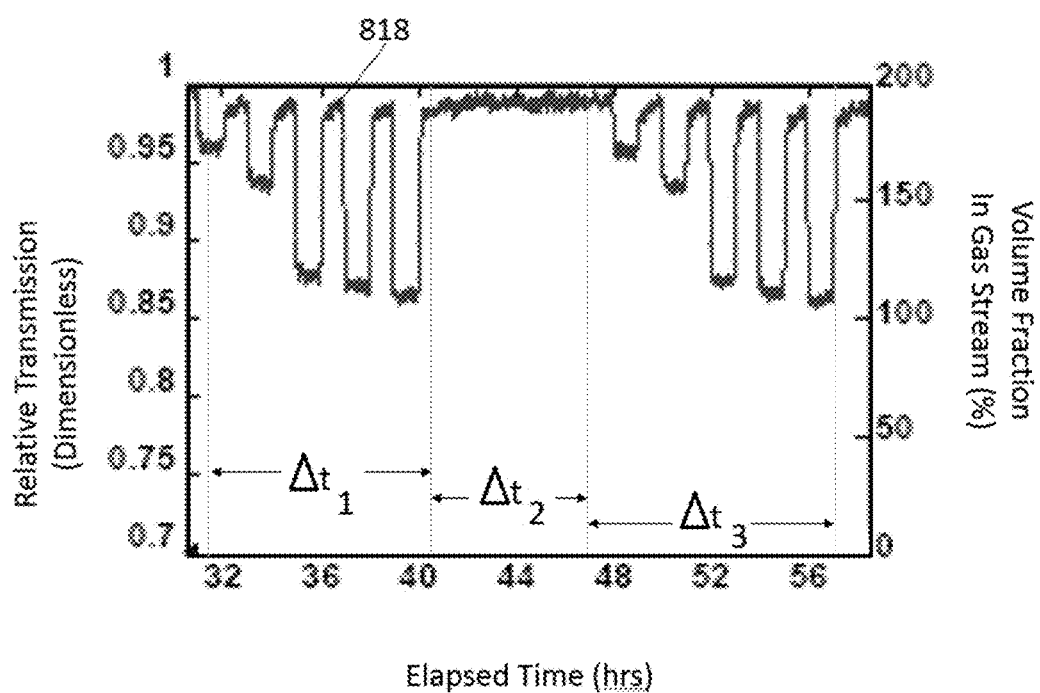
FIG. 8 illustrates an optical signal in the presence of $H_2$ and CO.

FIG. 7 illustrates the performance of a $Pd/SiO_2$ hydrogen sensing material in the presence of $H_2$, CO, and $O_2$. At FIG. 7, a 20% $O_2$ background was maintained over time periods $\Delta t_1$, $\Delta t_2$, and $\Delta t_3$, while $H_2$ was varied with an absence of CO over time period $\Delta t_1$, CO was varied with an absence of $H_2$ over time period $\Delta t_2$, and $H_2$ was varied in the presence of 1% CO over time period $\Delta t_3$. Optical signal 717 illustrates the response of the $Pd/SiO_2$ hydrogen sensing material at a wavelength of 525 nm. As illustrated, the hydrogen sensing response of the $Pd/SiO_2$ hydrogen sensing material remains in the simultaneous presence of $O_2$, CO, and $H_2$. As an additional example, FIG. 8 illustrates the performance of the $Pd/SiO_2$ hydrogen sensing material in the presence of $H_2$ and CO with optical signal 818, generated while $H_2$ varied with an absence of CO over time period $\Delta t_1$, CO varied with an absence of $H_2$ over time period $\Delta t_2$, and $H_2$ varied in the presence of 1% CO over time period $\Delta t_3$. See Ohodnicki et al., *Sensors and Actuators B* 214 (2015), which is incorporated herein by reference.

Figure 12A:
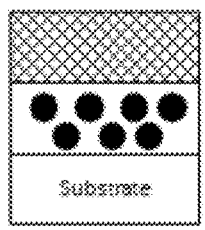
FIG. 12A illustrates additional exemplary structure of sensing layers comprised of zeolitic filter overlayer for a nanocomposite-based Pt- or Pd-nanoparticle layer.
Figure 12B:
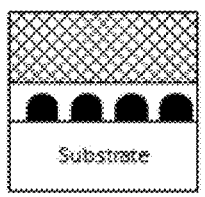
FIG. 12B illustrates additional exemplary structure of sensing layers comprised of a zeolitic layer on top of Pd- or Pt-based nanoparticles deposited directly on a substrate.
Figure 12C:
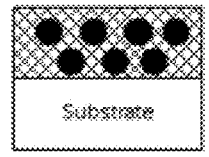
FIG. 12C illustrates additional exemplary structure of sensing layers comprised of a nanocomposite film comprised of Pd-nanoparticles or Pt-nanoparticles embedded within the zeolitic layer.
Figure 12D:
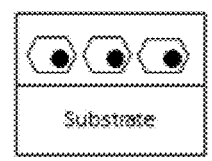
FIG. 12D illustrates additional exemplary structure of sensing layers comprised of (4) a layer comprised of core-shell particles with a core of Pd- or Pt-based nanoparticles and an outer shell comprised of a zeolitic (or other inert matrix) layer, and any combinations of the above.

FIG. 12A illustrates additional exemplary structures of sensing layers may be comprised of zeolitic filter overlayer for a nanocomposite-based Pt- or Pd-nanoparticle layer, FIG. 12B illustrates additional exemplary structures of sensing layers may be comprised of (a zeolitic layer on top of Pd- or Pt-based nanoparticles deposited directly on a substrate, FIG. 12C illustrates additional exemplary structures of sensing layers may be comprised of a nanocomposite film comprised of Pd-nanoparticles or Pt-nanoparticles embedded within the zeolitic layer, FIG. 12D illustrates additional exemplary structures of sensing layers may be comprised of a layer comprised of core-shell particles with a core of Pd- or Pt-based nanoparticles and an outer shell comprised of a zeolitic (or other inert matrix) layer, and any combinations of the above.

Figure 13:
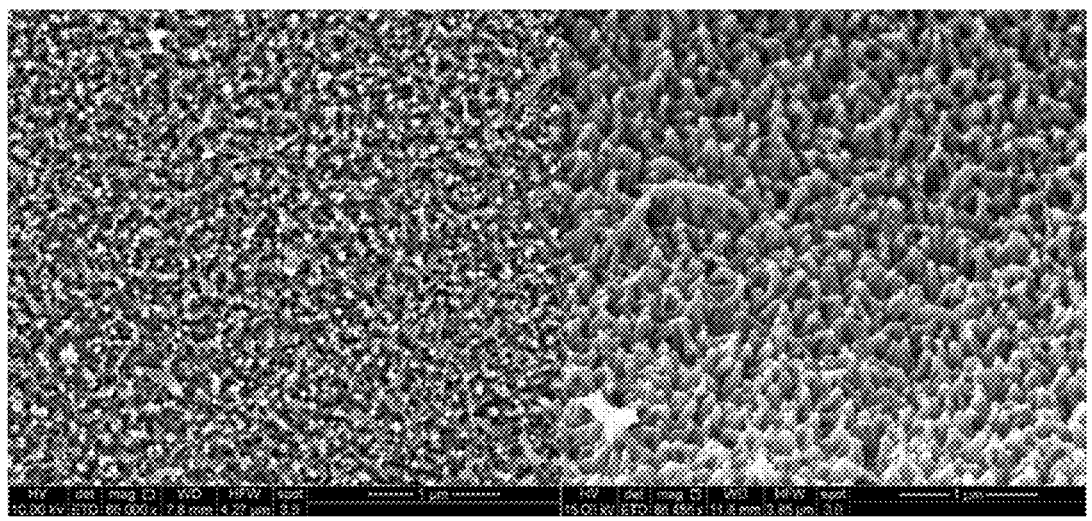
FIG. 13 illustrates SEM images of polyaniline nanofibers.

FIG. 13 illustrates an alternative matrix structure comprised of polyaniline nanofibers, which were prepared by in-situ polymerization. PANI is not only a gas sensitive material but also used as the porous matrix that brings about good dispersion quality of the Pt- or Pd-nanoparticles.

FIGS. 14A-14C illustrates example images of a multi-layered sensing layer comprised of a zeolitic-derivative filter layer deposited on a Pd—SiO2 based sensing layer. FIG. 14A is the STEM HAADF image of the cross section of the as-made fiber sample showing the distinctive textures of the double-layer. The top thick Pt layer was deposited during FIB lift-out process to protect fiber surface from damage by Ga ion beam. The layer with a thickness of ~50 nm underneath Pt was identified as zeolite nanoblocks layer by EDS (FIG. 14B). The layer underneath the filter layer with a thickness of ~65 nm was identified as $Pd/SiO_2$ layer by EDS as well as HRTEM image (FIG. 14C and inset), where the nanoparticles can be assigned to Pd with cubic crystal structure with a lattice constant of 3.89 Å. The bottom layer is $SiO_2$ from the core of the fiber sample.

The XRD pattern of original NaA crystals in FIG. 15B showed the presence of highly crystalline Linde Type A (LTA) type structure. After dissolution in the HCl solution, all characteristic peaks disappeared in FIG. 15A which indicates the amorphization of the crystalline structure. It has been reported that the acid treatment selectively removes Al atoms from the zeolites framework and this removal results in structural collapse and amorphous silicate species. From the above SEM and XRD results, we can infer these silica-rich nano-blocks have a size of a few nm and contain 4- and 6-membered rings with aluminum nanoparticles embedded, which generates small pores for only $H_2$ permeation.

Figures 16A, 16B:
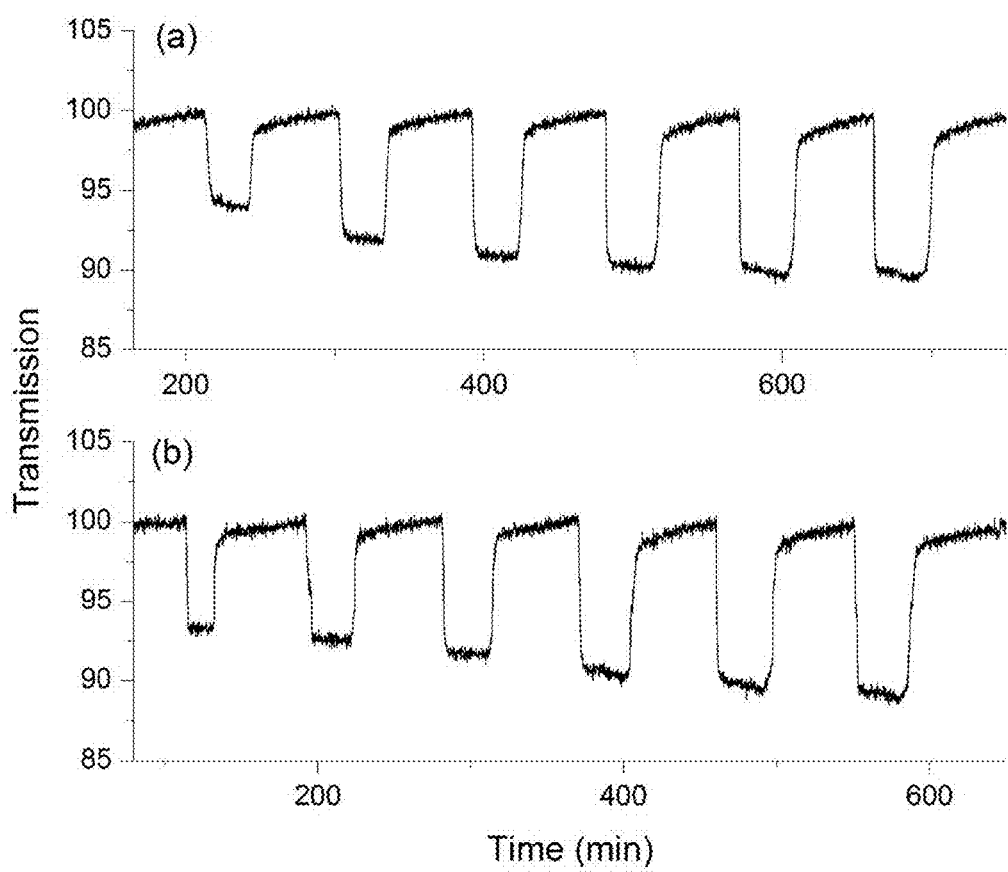
FIG. 16A illustrates measured sensing responses to high concentrations of $H_2$ (5%, 10%, 20%, 50%, 80%, 100%) in a balance of UHP $N_2$ for a 600° C. calcined Pd/$SiO_2$ optical fiber sensor without zeolites nano-blocks film.
FIG. 16B illustrates measured sensing responses to high concentrations of $H_2$ (5%, 10%, 20%, 50%, 80%, 100%) in a balance of UHP $N_2$ for a 600° C. calcined Pd/$SiO_2$ optical fiber sensor with zeolites nano-blocks film.
Figures 17A, 17B:
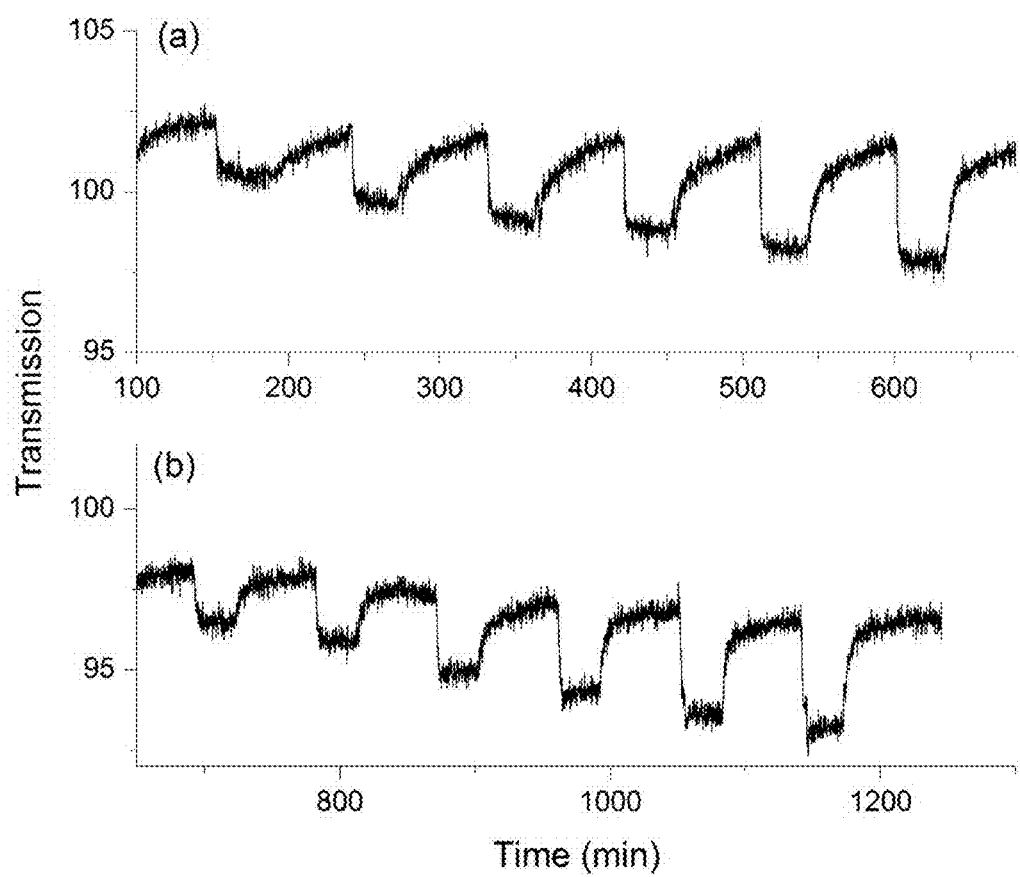
FIG. 17A illustrates measured sensing responses to low concentrations of $H_2$ (100 ppm, 200 ppm, 500 ppm, 1000 ppm, 1500 ppm, 2000 ppm) in a balance of UHP $N_2$ for a 600° C. calcined Pd/$SiO_2$ optical fiber sensor without zeolites nano-blocks film.
FIG. 17B illustrates measured sensing responses to low concentrations of $H_2$ (100 ppm, 200 ppm, 500 ppm, 1000 ppm, 1500 ppm, 2000 ppm) in a balance of UHP $N_2$ for a 600° C. calcined Pd/$SiO_2$ optical fiber sensor with zeolites nano-blocks film.

After coating with the zeolites filter layer, the sensing responses was evaluated in the presence of a broad range of $H_2$ concentrations and it was confirmed that the monotonic $H_2$ sensing responses could be retained without significant reduction in absolute sensitivity. FIG. 16 shows the normalized transmission responses at a wavelength of 500 nm to high concentrations of $H_2$ from 1% to 10% by volume balanced with $N_2$. For a potential extension of this class of sensor materials to low level $H_2$ detection and quantification in applications such as dissolved gas analysis monitoring, responses must be characterized in greater detail at relatively lower levels of $H_2$ from ~100 ppm to 0.5%. As a result responses in this range were probed experimentally as well, and monotonic responses were observed with reasonable response and recovery times as shown in FIG. 17. These sensing results indicate that this $H_2$ sensor approach is relevant for both leak detection at levels ranging up to and above the lower explosive limit as well as dissolved gas analysis of insulation oils at ppm-range levels such as for power transformer monitoring applications.

Figure 18A:
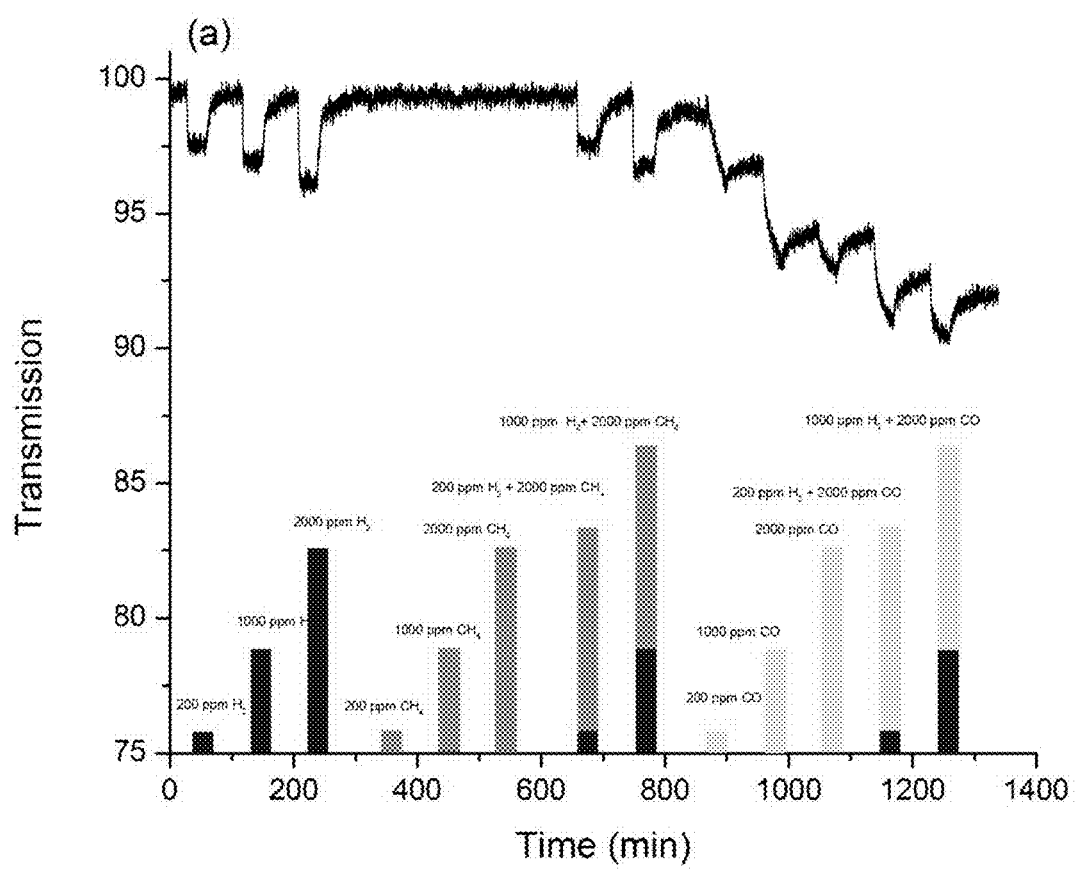
FIG. 18A illustrates measured sensing responses to $H_2$, $CH_4$, mixture of $H_2$ and $CH_4$, CO, mixture of $H_2$ and CO without zeolites nano-blocks film.
Figure 18B:
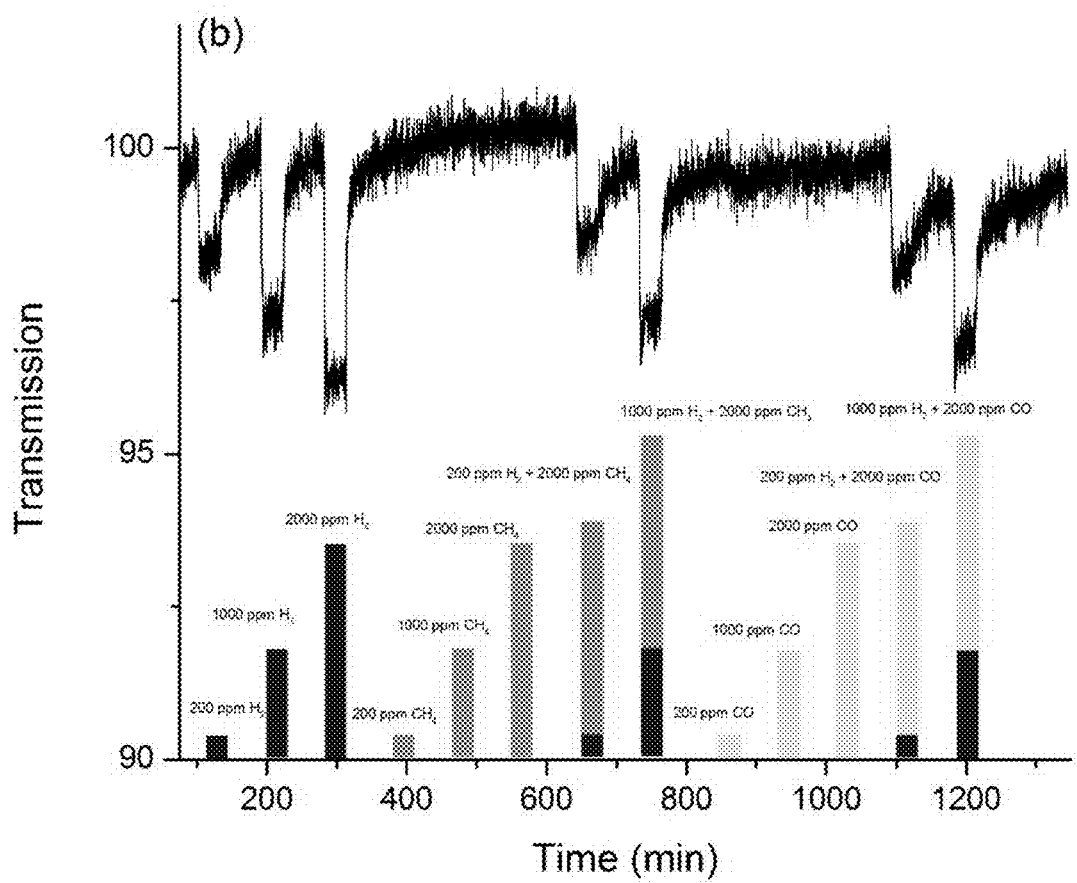
FIG. 18B illustrates measured sensing responses to $H_2$, $CH_4$, mixture of $H_2$ and $CH_4$, CO, mixture of $H_2$ and CO without zeolites nano-blocks film with zeolites nano-blocks film.

Experiments were therefore performed to study the sensitivity of the $Pd/SiO_2$ based sensing layers to typical concentrations of $CH_4$ and CO presented in gas blankets over transformer oils before and after overcoating with a filter layer. As shown in FIG. 18A, no measurable response was observed for $CH_4$ but in the presence of CO, considerable responses were observed and the $N_2$ purge could not recover to the original baseline without the filter layer. This is because CO desorption does not take place at RT, which do result in a strong interference towards $H_2$. Experiments were then repeated after coating of the $Pd/SiO_2$ sensor element with the zeolite based filter layer. FIG. 18B shows the sensor retained the insensitivity to $CH_4$ at room temperature and a minimization of the observed CO interferences for the $Pd/SiO_2$ sensing layer without the zeolite coating. A lack of cross-sensitivity to $CH_4$ is not unexpected as $CH_4$ does not tend to react with Pd-based sensing layers at temperatures lower than ~350-400° C. due to its thermodynamic stability. The improvement of interferences to CO through application of the zeolite-based filter layer can be attributed to the inherent molecular sieving capability of the zeolites nanoblocks. Both CO and $CH_4$ have kinetic diameters much larger than that of $H_2$ and can be blocked from interacting with the underlying sensor layer due to the small zeolite channels allowing only significant levels of $H_2$ permeance.

Hydrogen sensing material 101 is comprised of a plurality of Pd-based nanoparticles, Pt-based nanoparticles, and combinations thereof dispersed in an inert matrix, where the Pd-based nanoparticles comprise palladium (Pd), a palladium alloy, or combinations thereof, and where the Pt-based nanoparticles comprise platinum (Pt), a platinum alloy, or combinations thereof. In an embodiment, the palladium alloy is a palladium-silver alloy, a palladium-copper alloy, a palladium-platinum alloy, or combinations thereof, and in another embodiment the platinum alloy is a platinum-silver alloy, a platinum-copper alloy or combinations thereof. In an embodiment, a metallic component comprises at least 50 wt. %, preferably at least 70 wt. %, more preferably at least 90 wt. % of the plurality of nanoparticles, where the metallic component consists of one of palladium, platinum, a palladium alloy, a platinum alloy, and combinations thereof. In another embodiment at least 30 wt. % and in a further embodiment at least 50 wt. % of the metallic component consists of palladium, platinum, or combinations thereof. Here, palladium alloy means a stoichiometric or non-stoichiometric solid solution of palladium and an alloying element. In an embodiment, at least 30 wt. % of the palladium alloy consists of palladium, and in a further embodiment at least 50 wt. % of the palladium alloy consists of palladium. Similarly, platinum alloy means a stoichiometric or non-stoichiometric solid solution of platinum and an alloying element. In an embodiment, at least 30 wt. % of the platinum alloy consists of platinum, and in a further embodiment at least 50 wt. % of the platinum alloy consists of platinum. Additionally, the plurality of Pd-based nanoparticles, Pt-based nanoparticles, and combinations thereof have an average nanoparticle diameter of less than about 100 nanometers. In an embodiment, the average nanoparticle diameter is less than 10 nanometers, and in another embodiment, less than 5 nanometers. The average size of the Pd-based and Pt-based nanoparticles may be tailored in order to derive a desired response. For example, relatively large particles approaching 100 nm in diameter may strongly scatter light in the visible range while relatively small particles less than approximately 10-20 nm may not. In some embodiments, nanoparticle diameters less than 10 nanometers may be utilized to provoke absorption based responses to avoid potential interference from background light coupled into the $H_2$ sensing material. Tailoring the particle size can therefore affect the wavelength and optical response of a metallic nanoparticle extinction, absorption, and scattering cross-section. In an embodiment, the average nanoparticle diameter is greater than about 2 nm. The average nanoparticle diameter may be determined using various methods known in the art for the sizing of nanoparticles, for example, scanning electron microscopy (SEM), atomic force microscopy (AFM), and transmission electron microscopy (TEM) methods. Preferably, the average particle size is determined through image analysis by capturing a sample of typically at least 100 nanoparticles, more preferably at least 300 nanoparticles. However, as is understood, the method by which an average nanoparticle diameter is determined is not limiting within this method.

It is understood that the nanoparticles of this disclosure are not limited to strictly spherical shapes, and that the plurality of gold nanoparticles may be comprised of shapes such as triangular prisms, disks, shells, wires, rods, and others. When such structures are present, the average particle diameter refers and is equivalent to an equivalent circular diameter (ECD), which connotes the diameter of a circle with area equal to that of the projection of the particle on a plane. See e.g., Xu et al, "Comparison of sizing small particles using different technologies," *Powder Technology* 132 (2003).

Additionally, the inert matrix has a bandgap greater than or equal to 5 eV, and has an oxygen ion conductivity less than approximately $10^{-7}$ S/cm at a temperature of 700° C., where the oxygen ion conductivity is either known from compiled sources or determined using techniques known in the art, such as the oxygen permeation method. See e.g. Kagomiya et al., "Oxygen permeation and microstructure of intergrowth perovskite Sr—La—Fe—Co based mixed conductive ceramics," *J. Ceram. Soc. Jpn.* 117 (9) (2009); and see Chen et al., "Ionic conductivity of perovskite $LaCoO_3$ measured by oxygen permeation technique," *J. Appl. Electrochem.* 27 (1997), among others. The inert matrix is generally based upon a stoichiometric dielectric material, such as $SiO_2$, $Si_3N_4$, or $Al_2O_3$. In an embodiment, the matrix material comprises an inorganic metal oxide of the formula MaOb, where M comprises one or more metals. In some cases, the inert matrix may consist of more complex systems such as $MgF_2$-doped $SiO_2$, or mixed $SiO_2/Al_2O_3$ to tailor the effective refractive indices for optimized sensing response in optical waveguide based sensing applications.

In some embodiments, microporous or nanoporous zeolites such as Faujasite (FAU), Pentasil (MFI), Linde Type A (LTA), Mordenite (MOR), Chabazite (CHA), and any other dealuminated zeolites are used as overlayers or matrix materials. They are particularly adapted for supporting nanoparticles both in microporous cavities of the framework and in mesoporous channels. For example, metal nanoparticles are protected against poisoning or sintering by a thin zeolite shell. A large internal void is available for chemical reactions and such core-shell structures can be considered as nanoreactors in which the reaction is essentially governed by the permeability of the shell. Depending on the preparation method, the encapsulation of nanoparticles in zeolites may be categorized into various architectures, such as (1) NPs in hollow zeolite single crystals, (2) NPs in polycrystalline zeolite shells, (3) NPs inside or between zeolite nanosheets or plates, (4) NPs in zeolite framework cavities or pores, and (5) NPs in intercrystalline mesopores.

In an alternative matrix materials that do not fall within the classification of inert oxides claimed within the current application may comprise three-dimensional (3D) hierarchical carbon materials such as graphene assemblies, carbon nanotube networks and activated carbon. The interconnected 3D multilayered structures provide promising properties, such as high surface area, a distinct 3D porous network, and a facile electron transport ability. For example, the macroporosity of 3D graphene allows deposition of a high surface area of catalytic NPs and along with the nanosize dimensions of the connecting arms and nodes provides a highly favourable mass transport environment for delivery of analytes which will be useful for enhancing diverse catalytic and sensing processes.

An additional class of alternative matrix materials that do not fall within the classification of inert oxides claimed within the current application may comprise conducting polymers, such as polypyrrole (PPy), polyaniline (PANT), polythiophene (PTh), and their derivatives. Conducting polymers have many interesting characteristics for sensing including their high sensitivity, short response time, and the possibility of tuning both chemical and physical properties by using different substituents; especially, these features are ensured at room temperature. For example, the use of nanostructured polyaniline (such as nanowires, nanotubes, nanofibers, or nanorods) could greatly improve diffusion, favoring much greater penetration depth for gas molecules, relative to their bulk counterparts.

An inert matrix as defined within this disclosure has limited free carriers, and can be expected to display negligible change in refractive index in response to reducing species that may occur in a monitored stream even at the high temperature conditions of interest relevant for this disclosure. Additionally, the inert matrix acts to mitigate the coarsening of Pd-based or Pt-based nanoparticles which might otherwise occur under the high temperature conditions of this disclosure. In some embodiments the inert matrix may act to prevent oxidation and/or reduction of the Pd-based and/or Pt-based nanoparticles thereby increasing selectivity to $H_2$ in a broad range of atmospheres. In other embodiments, oxidation and reduction reactions may be permitted and desirable for an optimized sensing response.

The inert matrix supporting the plurality of Pd-based and/or Pt-based nanoparticles is permeable at least to some degree to the incident light at wavelengths corresponding to the wavelength or wavelength range over which the optical signal generates. For example, when optical signals are generated within a light wavelength range from about 300 nm to about 850 nm or a smaller range, the inert matrix is permeable at least to some degree to the incident light at wavelengths from about 300 nm to about 850 nm or within the smaller range. Similarly, when optical signals generate within a light wavelength range from about 1350 nm to about 1750 nm or a smaller range, the inert matrix is permeable at least to some degree to the incident light at wavelengths from about 1350 nm to about 1750 nm or within the smaller range. In an embodiment, the inert matrix is permeable at least to some degree to light at wavelengths over the visible spectrum. Here "visible spectrum" connotes light having wavelengths from about 400 nm to about 750 nm. The optical properties of the inert matrix are such that the inert matrix has a refractive index greater than one. In some embodiments, the inert matrix has an extinction coefficient of less than $10^{-5}$ $cm^{-1}$ over the wavelength range of interrogation, and in other embodiments, the inert matrix has an extinction coefficient of less than $10^{-3}$ $cm^{-1}$ over the wavelength range of interrogation.

As discussed, within hydrogen sensing material 101, the Pd-based nanoparticles, Pt-based nanoparticles, and combinations thereof are dispersed in the inert matrix. As used herein, "dispersed" means that individual nanoparticles comprising the plurality of Pd-based nanoparticles, Pt-based nanoparticles, and combinations thereof in hydrogen sensing material 101 are sufficiently separated such that hydrogen sensing material 101 displays an electrical conductance at least an order of magnitude less than the electrical conductance of a bulk material comprised of the same material as the Pd and/or Pt-based nanoparticles under an equivalent temperature condition, such that the electrical conductance is less than $1/10^{th}$ of the electrical conductance of the bulk material. Such a condition can be determined using various methods for the evaluation of proximity to a percolation limit in supported nanoparticle systems. See e.g. Trudeau et al., "Competitive transport and percolation in disordered arrays of molecularly linked Au nanoparticles," *J. Chem. Phys.*, Vol. 117 (2002), among others. Additionally, in an embodiment, an average spacing between individual Pd and/or Pt-based is at least five times greater than the average nanoparticle diameter, where average spacing indicates the average displacement between a given nanoparticle and a nearest nanoparticle neighbor. For the given nanoparticle, the nearest nanoparticle neighbor may be determined through a variety of statistical methods known in the art, such as fixed radius analysis, minimal spanning trees, Voronoi polygons, k-nearest neighbor algorithms, and other established nearest neighbor methodologies. See e.g., Dussert et al., "Minimal spanning tree: A new approach for studying order and disorder," *Phys. Rev. B,* 34 (5) (1986), and see Aurenhammer, "Voronoi Diagrams—A Survey of a Fundamental Geometric Data Structure," *ACM Comput. Surv.,* 23(3) (1991), and see Cover et al., "Nearest Neighbor Pattern Classification," *IEEE T Inform. Theory* 13(1) (1967), among others. The displacement between the given nanoparticle and the nearest nanoparticle neighbor may be determined using techniques such as scanning electron microscopy, atomic force microscopy, and transmission electron microscopy, and the average spacing may be determined as the average value over some statistically significant population of Pd and/or Pt-based nanoparticles, for example at least 100 nanoparticles.

Figure 9:
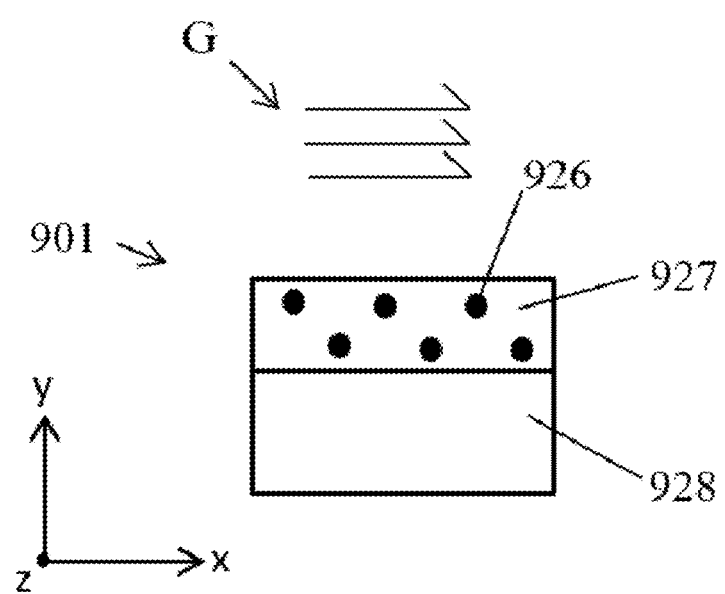
FIG. 9 illustrates an additional embodiment of the hydrogen sensing material.
Figure 10:
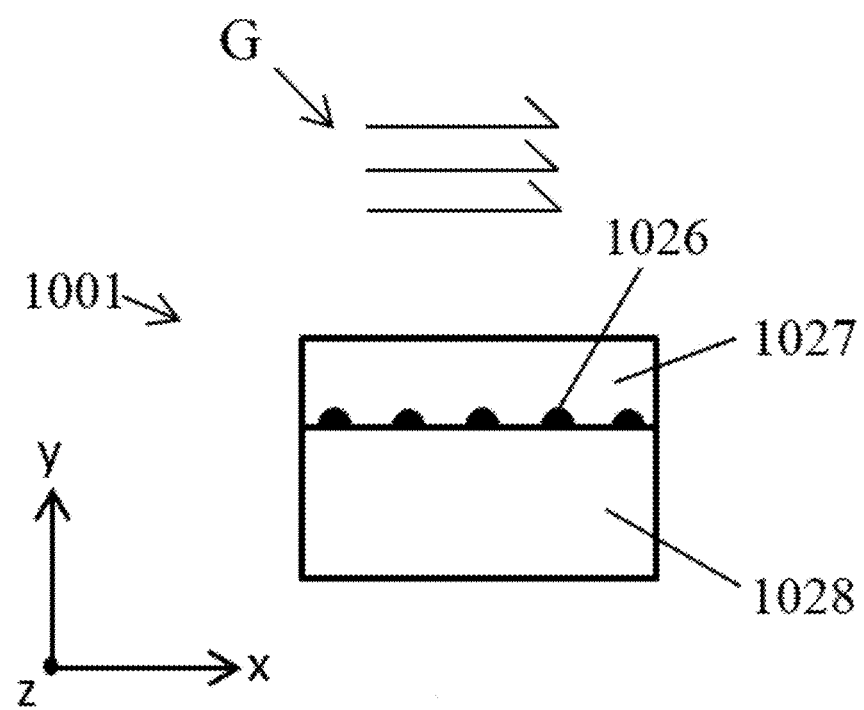
FIG. 10 illustrates an additional embodiment of the hydrogen sensing material.

The Pd and/or Pt-based nanoparticles may be dispersed relatively uniformly or non-uniformly with respect to the inert matrix, provided that the nanoparticles are dispersed within the meaning of the definition discussed above. For example, FIG. 9 illustrates hydrogen sensing material 901 in contact with gas stream G, where hydrogen sensing material 901 comprises a plurality of Pd-based nanoparticles, Pt-based nanoparticles, and combinations thereof such as nanoparticle 926 within inert matrix 927, and where hydrogen sensing material 901 is further in contact with a substrate 928. At FIG. 9, the plurality of Pd and/or Pt-based nanoparticles are distributed relatively homogenously through inert matrix 927, such that the relative concentration of Pd and/or Pt-based nanoparticles is substantially similar within inert matrix 927 as displacement occurs in a negative direction of the y-axis illustrated. In an embodiment, a majority of a statistically significant population of Pd-based nanoparticles, Pt-based nanoparticles, and combinations thereof are within inert matrix 927 such that at least some portion of inert matrix 927 is between the majority and gas stream G. Similarly, FIG. 10 illustrates hydrogen sensing material 1001 in contact with gas stream G, where hydrogen sensing material 1001 comprises a plurality of Pd-based nanoparticles, Pt-based nanoparticles, and combinations thereof such as nanoparticle 1026 within inert matrix 1027, and where hydrogen sensing material 1001 is further in contact with a substrate 1028. FIG. 10 depicts the plurality of Pd and/or Pt-based nanoparticles concentrated in a region of inert matrix 1027 such that the relative concentration of nanoparticles increases within inert matrix 1027 as displacement occurs in a negative direction of the y-axis illustrated, and decreases or disappears as displacement occurs in a positive direction of the y-axis illustrated. However, arrangements such as those in FIGS. 9 and 10 are exemplary only, and the relative concentrations of Pd-based nanoparticles in varying regions of the inert matrix are not limiting within this disclosure provided the plurality of Pd-based nanoparticles, Pt-based nanoparticles, and combinations thereof are dispersed within the inert matrix as discussed above.

Additionally, it is understood that when the disclosure describes monitoring an optical signal and thereby evaluating the hydrogen concentration of the gas stream, this includes operations where a shift in the optical signal serves as an indication of a change in the hydrogen concentration of the gas stream. As an example using the results of FIG. 3 for the hydrogen sensing material of $Pd/SiO_2$, the hydrogen sensing material generates the optical signal 310 at a first magnitude $A_1$ at an $H_2$ concentration of 2% and at a second magnitude $A_2$ at an $H_2$ concentration of 10%. Here, evaluating the hydrogen concentration of the gas stream may comprise treating the first magnitude $A_1$ as a measurand and assigning a specific value of $H_2$ to the measurand such as 2%, or may comprise monitoring the optical signal at one or more wavelengths, observing a shift in the optical signal such as from $A_1$ to $A_2$, and treating the observed shift as indicative of a change in $H_2$. Here, a "shift in the optical signal" means a variation between an initial optical signal and a subsequent optical signal at one or more wavelengths, where the initial optical signal is generated at a first time and the subsequent optical signal is generated at a second time, and where both the initial optical signal and the subsequent optical signal are generated by illuminating the hydrogen sensing material with the light source emitting the incident light, collecting the exiting light, and comparing the incident light and the exiting light using optical spectroscopy. The shift in the optical signal may be recognized by detecting a variation between optical signals at any monitored wavelength or by variations at multiple wavelengths over a band of wavelengths. For example, the variation may be detected by monitoring a transmittance at a specific wavelength, the specific wavelength of an optical signal edge within a specified wave length range, the wavelength of an optical signal local maxima, a variation in the optical signal breadth, a variation in the optical signal amplitude, a variation in the optical signal full width at half maximum (FWHM), or any other techniques which may serve to indicate a variation between the initial optical signal and a subsequent optical signal. In an embodiment, the shift in the optical signal means a variation of at least 0.1% between an initial time-averaged optical signal and a subsequent time-averaged optical signal in transmittance, absorptance, or reflectance at a specific wavelength.

Figure 19A:
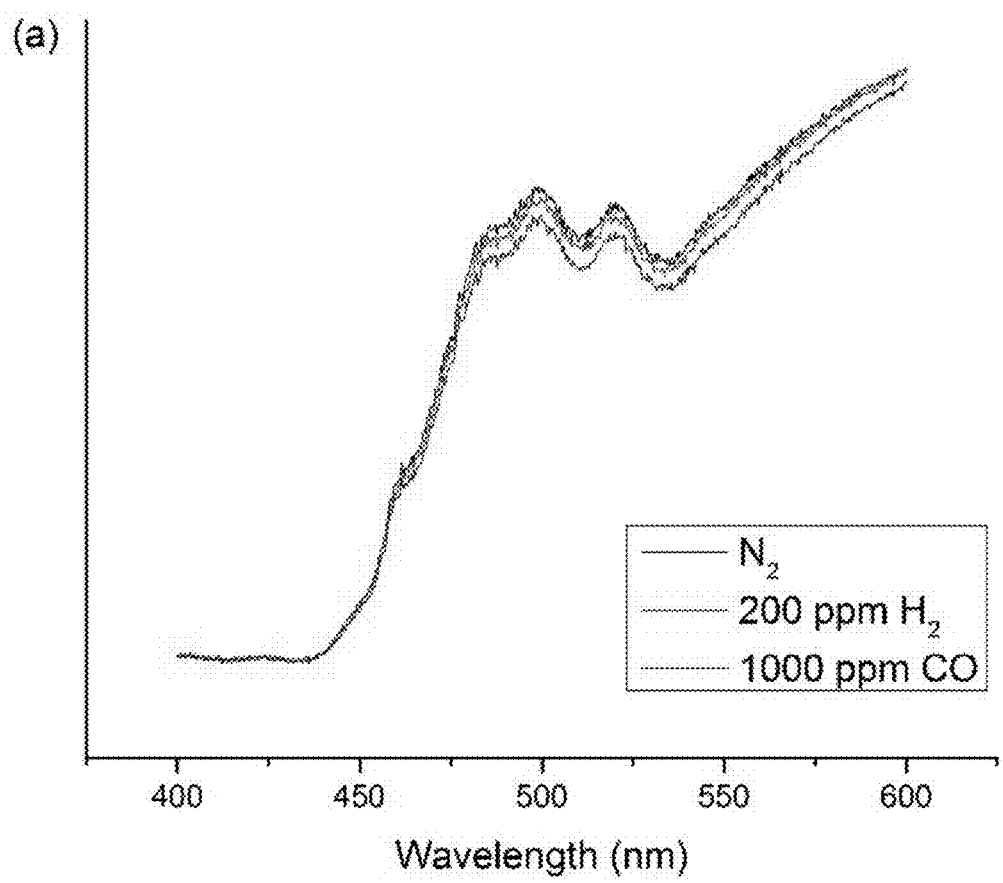
FIGS. 19A and 19B illustrate transmission spectrum for measured sensing responses to $H_2$ and CO.
Figure 19B:
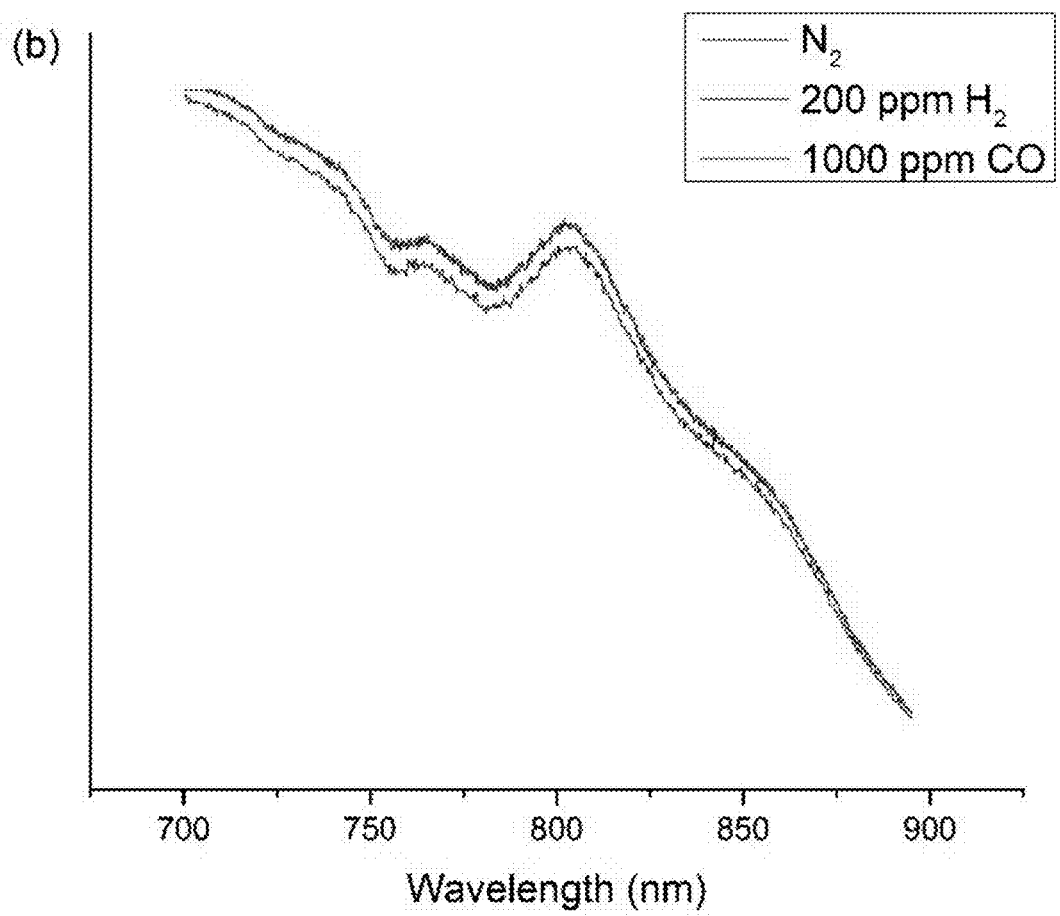

Optical fiber sensors also handle multiplexed sensing and allow for spatially resolved monitoring of various parameters through distributed interrogation methodologies. In some cases, different analytes may result in unique spectral responses within the UV-Vis and NIR regions and would be good candidates for multi-wavelength referencing for fiber optical sensors, which makes mapping different gas species possible. For example, $H_2$ and CO have been observed to provide unique spectroscopic features of the analytes for Pd nanoparticle incorporated SiO2 films. In FIG. 19a, the transmission spectrum shows distinctive features for $N_2$, CO and $H_2$ in the 450-550 nm region for a Pd nanoparticle incorporated SiO2 film sensing layer at room temperature. In FIG. 19b, the spectrum exhibits intensity change between 700-900 nm only in the presence of CO, while the spectrum of $N_2$ and $H_2$ overlaps. Using unique spectral signatures associated with different analytes such as those presented here for Pd nanoparticle incorporated $SiO_2$ films, it can be possible to distinguish unique analytes through multiple wavelength interrogation.

Figure 11:
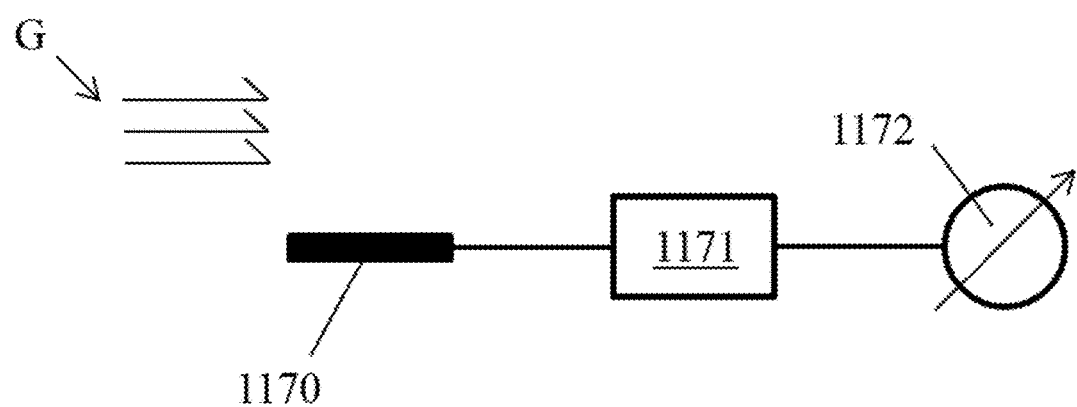
FIG. 11 illustrates an instrument using the hydrogen sensing material.

In a particular embodiment, the hydrogen sensing material is employed in an instrument such as that illustrated at FIG. 11. In this embodiment, the hydrogen sensing material of this disclosure comprises a sensing head 1170 in contact with a gas stream G. An interrogator 1171 illuminates the hydrogen sensing material comprising sensing head 1170 with incident light and gathers exiting light. Interrogator 1171 compares the incident light and the exiting light and generates a measurand, where the measurand is proportional to the optical signal as defined herein. Such interrogators for use in optical systems are known in the art. See e.g., Lee et al., "Review of the present status of optical fiber sensors," Optical Fiber Technology 9 (2003), and associated references. Interrogator 1171 is in data communication with meter 1172 which provides an indication of the magnitude of the measurand generated and communicated by interrogator 1171. In this embodiment, the steps of illuminating the hydrogen sensing material, collecting exiting light, and monitoring an optical signal based on a comparison of the incident light and the exiting light is conducted by interrogator 1171, and monitoring the optical signal is conducted through observation of meter 1172. An indication of the $H_2$ concentration of gas stream G is provided by comparison of the observed meter reading and a reference meter reading, where the reference meter reading results from a reference measurand generated under reference conditions.

The hydrogen sensing material utilized in the method of this disclosure may be prepared using means known in the art for the production of gold nanoparticles dispersed in a supporting matrix, including sol-gel wet chemistry based techniques, impregnation techniques, implantation techniques, sputtering techniques, and others. See e.g. Ohodnicki et al., "$Pd/SiO_2$ and $AuPd/SiO_2$ nanocomposite-based optical fiber sensors for $H_2$ sensing applications," *Sensors and Actuators B* 214 (2015). Generally, rigorous calcination schedules will improve the temperature stability of the resulting material under the reducing conditions of this disclosure. A high calcination temperature and long calcination time may ensure that the resulting hydrogen sensing material is properly aged, so that any optical property changes occurring in the material during sensing operations at the higher temperatures of this disclosure can be attributed to $H_2$ concentration of the monitored stream. However, the specific manner in which the hydrogen sensing material of this disclosure is prepared is not limiting within this disclosure, provided that the hydrogen sensing material is comprised of Pd-based nanoparticles dispersed in an inert matrix as defined herein.

Thus, provided here is a method for $H_2$ sensing in a gas stream which utilizes an optical signal generated by a hydrogen sensing material. The hydrogen sensing material is comprised of a plurality of Pd-based nanoparticles, Pt-based nanoparticles, and combinations thereof dispersed in a wide bandgap matrix with a low oxygen ion conductivity. The method disclosed offers significant advantage over materials typically utilized for $H_2$ sensing, including enhanced thermal stability, relative insensitivity to reducing gases beyond $H_2$, increased stability of nanoparticle diameter, tunability of effective refractive indices for compatibility with optical waveguide based sensors, among others.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

What is claimed is:

1. A method of evaluating a hydrogen concentration of a gas stream comprising:
   placing a hydrogen sensing material in the gas stream, where the hydrogen sensing material comprises:
   an inert matrix, where the inert matrix is stable at the gas stream temperature, and where the inert matrix is optically transparent over a light wavelength range, and where the inert matrix has a bandgap greater than or equal to 5 eV and has an oxygen ion conductivity of less than $10^7$S/cm at a temperature of 700° C.,
   a plurality of nanoparticles dispersed in the inert matrix, where the plurality of nanoparticles comprises at least one of Pd-based nanoparticles, Pt-based nanoparticles, and combinations thereof, and where an individual nanoparticle in the plurality of nanoparticles comprises palladium, platinum, a palladium alloy, or a platinum alloy, and where the plurality of nanoparticles have an average nanoparticle diameter of less than about 100 nanometers;
   illuminating the hydrogen sensing material with a light source emitting incident light; collecting exiting light, where the exiting light is light that originates at the light source and is transmitted, reflected, scattered or a combination thereof by the hydrogen sensing material;
   monitoring an optical signal based on a comparison of the incident light and the exiting light using optical spectroscopy, thereby evaluating the hydrogen concentration of the gas stream.

2. The method of claim 1 where the palladium alloy comprises a palladium-silver alloy, a palladium-platinum alloy, and combinations thereof.

3. The method of claim 1 where the platinum alloy comprises a platinum-silver alloy.

4. The method of claim 1 where the average nanoparticle diameter is less than about 10 nanometers.

5. The method of claim 1 where the matrix layer is comprised of a zeolitic or zeolite-derived structures such as dealuminated zeolites.

6. The method of claim 1 where an overlayer of a matrix material is applied as a filter layer to improve the response.

7. The method of claim 6 where the overlayer is zeolitic or zeolite-derived structure such as dealuminated zeolites.

8. The method of claim 6 where the overlayer is a nanoporous structured material which provides an inherent filtering function for analyte species.

9. The method of claim 1 where a metallic component comprises at least 50 wt. % of the plurality of nanoparticles, where the metallic component consists of one of the palladium, the platinum, the palladium alloy, the platinum alloy, and combinations thereof.

10. The method of claim 9 where the metallic component consists of one of the palladium, the palladium alloy, and combinations thereof.

11. The method of claim 9 where the metallic component consists of one of the platinum, the platinum alloy, and combinations thereof.

12. The method of claim 9 where the metallic component comprises at least 90 wt. % of the plurality of nanoparticles.

13. The method of claim 1 where the inert matrix comprises an inorganic metal oxide having a formula $M_aO_b$, where M comprises one or more metals.

14. The method of claim 13 where the inorganic metal oxide comprises at least 50 wt. % of the inert matrix.

15. The method of claim 14 where the inert matrix comprises one of $SiO_2$, $Al_2O_3$, $Si_3N_4$, or combinations thereof.

16. The method of claim 1 where the inert matrix is comprised of a zeolitic structure or a zeolite-derived structure such as a dealuminated zeolite.

17. The method of claim 1 where the sensing layer is comprised of a core-shell structure in which the Pd- or Pt-based nanoparticles are surrounded within a shell of the matrix layer.

18. The method of claim 17 where the matrix layer shell is comprised of a zeolitic structure or a zeolite-derived structure such as a dealuminated zeolite.

19. The method of claim 1 further comprising:
   providing a waveguide comprised of a core material;
   placing the hydrogen sensing material in contact with the core material; and
   emitting the incident light from the light source into the core material and illuminating the hydrogen sensing material, thereby illuminating the hydrogen sensing material with the light source emitting the incident light.

20. The method of claim 19 further comprising emitting the incident light from the light source into the core material and generating an evanescent wave in the hydrogen sensing material.

21. A method of evaluating the hydrogen concentration of the gas stream using the method of claim 1, further comprising:
   emitting incident light using an interrogator in optical communication with the hydrogen sensing material and illuminating the hydrogen sensing material, and gathering exiting light using the interrogator in optical communication with the hydrogen sensing material, and
   monitoring the optical signal based on the comparison of the incident light and the exiting light with optical spectroscopy using the interrogator, thereby illuminating the hydrogen sensing material with the light source emitting incident light, collecting exiting light, and monitoring the optical signal based on the comparison of the incident light and the exiting light using optical spectroscopy;

generating a measurand using the interrogator based on the optical signal, and communicating the measurand to a meter in data communication with the interrogator; and receiving the measurand at the meter and displaying a meter reading on the meter based on the measurand.

22. A method of evaluating a hydrogen concentration of a gas stream comprising: placing a hydrogen sensing material in the gas stream, where the hydrogen sensing material comprises, an inert matrix having an overlayer of a matrix layer applied thereto, where the inert matrix is stable at the gas stream temperature, and where the inert matrix is optically transparent over a light wavelength range, and where the inert matrix has a bandgap greater than or equal to 5 eV and has an oxygen ion conductivity of less than 10'S/cm at a temperature of 700° C., a plurality of nanoparticles dispersed in the inert matrix, where a metallic component comprises at least 50 wt. % of the plurality of nanoparticles, where the metallic component consists of one of palladium, platinum, a palladium alloy, a platinum alloy, and combinations thereof, and where the plurality of nanoparticles have an average nanoparticle diameter of less than about 10 nanometers;

illuminating the hydrogen sensing material with a light source emitting incident light; collecting exiting light, where the exiting light is light that originates at the light source and is transmitted, reflected, scattered or a combination thereof by the hydrogen sensing material;

monitoring an optical signal based on a comparison of the incident light and the exiting light using optical spectroscopy, thereby evaluating the hydrogen concentration of the gas stream.

23. The method of claim 22 where the inert matrix layer is comprised of a zeolitic or zeolite-derived structure such as a dealuminated zeolite.

24. The method of claim 22 further comprising:
providing a waveguide comprised of a core material;
placing the hydrogen sensing material in contact with the core material;
emitting the incident light from the light source into the core material and generating an evanescent wave; and
illuminating the hydrogen sensing material with the evanescent wave, thereby illuminating the hydrogen sensing material with the light source emitting the incident light.

* * * * *